US006632217B2

(12) United States Patent
Harper et al.

(10) Patent No.: US 6,632,217 B2
(45) Date of Patent: Oct. 14, 2003

(54) IMPLANTABLE OSMOTIC PUMP

(75) Inventors: Derek J. Harper, Goleta, CA (US); Charles F. Milo, Mountain View, CA (US)

(73) Assignee: MicroSolutions, Inc., Goleta, CA (US)

( * ) Notice: Subject to any disclaimer, the term of this patent is extended or adjusted under 35 U.S.C. 154(b) by 24 days.

(21) Appl. No.: 09/838,662

(22) Filed: Apr. 19, 2001

(65) Prior Publication Data

US 2002/0183722 A1 Dec. 5, 2002

(51) Int. Cl.[7] ................................................. A61K 9/22
(52) U.S. Cl. ................................ 604/892.1; 604/891.1
(58) Field of Search ........................... 604/891.1, 892.1, 604/65–67, 118, 122, 126, 131–133, 246, 256, 288.01, 288.04

(56) References Cited

U.S. PATENT DOCUMENTS

| | | | | | |
|---|---|---|---|---|---|
| 3,604,417 A | * | 9/1971 | Stolzenberg | ................ | 128/213 |
| 3,760,984 A | | 9/1973 | Theeuwes | | |

(List continued on next page.)

FOREIGN PATENT DOCUMENTS

| | | |
|---|---|---|
| WO | WO 00/54745 | 3/1999 |

OTHER PUBLICATIONS

F. Theewes et al, *Principles Of The Design and Operation Of Generic OsmoticPumps For The Delivery Of Semisolid Or Liquid Drug Formulations*, Annals Of Biomedical Engineering, 4, pp. 343–353, 1976.

Jon P. Monk, Rosemary Beresford and Alan Ward, *Sufentanil: A Review Of Its Pharmacological And therapeutic Use*, Drugs 36, pp. 286–313, 1988.

F.P. Boersma, M.D.; H. Noorduin, M.SC. and G. Vanden Bussche, M.D., *Epidural Sufentanil For Cancer Pain Control In Outpatients*, Regional Anestehesia, Nov.–Dec. vol. 14, No. 6, pp. 293–297, 1989.

Tim J. Lamer, M.D.; Symposium on Pain Management–Part II, *Treatment Of Cancer–Related Pain: When Orally Administered Medications Fail*, Mayo Clinic Proc., 69, pp. 473–480, 1994.

T.F. Meert and M. DeKock, *Potentiation Of The Analgesic Properties Of Fentanyl–Like Opioids With Alpha2–Adrenoceptor Agonists In Rats*, Anesthesiology, Sep., 81(3), pp. 677–688, 1994.

A. Paix, A. Coleman, J. Lees, J. Grigson, M. Brooksbank, D. Thorne and M. Ashby, *Subcutaneous Fentanyl And Sufentanil Infusion Substitution For Morphine Intolerance In Cancer Pain Management*, Pain, Nov.; 63(2), pp. 263–269, 1995.

F. Mercier, M. Dounas, H. Bouaziz, V. Des Mesnard–Smaja, C. Foiret, M.N. Vestermann, M. Fischler and D. Benhamou, *The Effect Of Adding A Minidose Of Clonidine To Intrathecal Sufentanil For Labor Analgesia*, Anesthesiology, Sep. 89(3), pp. 594–601, 1998.

(List continued on next page.)

*Primary Examiner*—Brian L. Casler
*Assistant Examiner*—Ann Y. Lam
(74) *Attorney, Agent, or Firm*—Young Law Firm, P.C.

(57) ABSTRACT

An implantable osmotic pump for delivering a pharmaceutical agent to a patient includes an osmotic engine, a substantially toroidal compartment disposed at least partially around the osmotic engine and a piston disposed within the compartment. The osmotic engine is configured to cause the piston to travel within the compartment and deliver a dose pharmaceutical agent contained within the compartment when the pump is implanted in an aqueous environment. A dose escalation assembly may be fitted to the pump, the dose escalation assembly being adapted to selectively increase the rate at which the pharmaceutical agent is delivered from the pump.

99 Claims, 18 Drawing Sheets

U.S. PATENT DOCUMENTS

| | | |
|---|---|---|
| 3,845,770 A | 11/1974 | Theeuwes |
| 3,916,899 A | 11/1975 | Theeuwes |
| 3,977,404 A | 8/1976 | Theeuwes |
| 3,987,790 A | 10/1976 | Eckenhoff |
| 4,008,719 A | 2/1977 | Theeuwes |
| 4,014,334 A | 3/1977 | Theeuwes |
| 4,031,891 A * | 6/1977 | Jess .......................... 128/214 |
| 4,034,758 A | 7/1977 | Theeuwes |
| 4,036,227 A | 7/1977 | Zaffaroni |
| 4,036,228 A | 7/1977 | Theeuwes |
| 4,058,122 A | 11/1977 | Theeuwes |
| 4,077,407 A | 3/1978 | Theeuwes |
| 4,093,708 A | 6/1978 | Zaffaroni |
| 4,096,238 A | 6/1978 | Zaffaroni |
| 4,111,201 A | 9/1978 | Theeuwes |
| 4,111,202 A | 9/1978 | Theeuwes |
| 4,111,203 A | 9/1978 | Theeuwes |
| 4,116,241 A | 9/1978 | Theeuwes |
| 4,135,514 A | 1/1979 | Zaffaroni |
| 4,142,526 A | 3/1979 | Zaffaroni |
| 4,160,020 A | 7/1979 | Ayer |
| 4,160,452 A | 7/1979 | Theeuwes |
| 4,193,398 A | 3/1980 | Refson |
| 4,200,098 A | 4/1980 | Ayer |
| 4,203,439 A | 5/1980 | Theeuwes |
| 4,256,108 A | 3/1981 | Theeuwes |
| 4,265,874 A | 5/1981 | Bonsen |
| 4,278,087 A | 7/1981 | Theeuwes |
| 4,285,987 A | 8/1981 | Ayer |
| 4,298,003 A | 11/1981 | Theeuwes |
| 4,327,725 A | 5/1982 | Cortese |
| 4,344,929 A | 8/1982 | Bonsen |
| 4,379,203 A * | 4/1983 | Koszytorz ................... 174/15 |
| 4,410,328 A | 10/1983 | Theeuwes |
| 4,449,983 A | 5/1984 | Cortese |
| 4,455,143 A | 6/1984 | Theeuwes |
| 4,455,145 A | 6/1984 | Theeuwes |
| 4,503,030 A | 3/1985 | Edgren |
| 4,552,561 A | 11/1985 | Eckenhoff |
| 4,576,604 A | 3/1986 | Guittard |
| 4,578,075 A | 3/1986 | Urquhart |
| 4,587,117 A | 5/1986 | Edgren |
| 4,608,048 A | 8/1986 | Cortese |
| 4,610,686 A | 9/1986 | Ayer |
| 4,612,008 A | 9/1986 | Wong |
| 4,615,698 A | 10/1986 | Guittard |
| 4,619,652 A | 10/1986 | Eckenhoff |
| 4,627,850 A | 12/1986 | Deters |
| 4,627,851 A | 12/1986 | Wong |
| 4,655,766 A | 4/1987 | Theeuwes |
| 4,673,405 A | 6/1987 | Guittard |
| 4,685,918 A | 8/1987 | Amidon |
| 4,705,515 A | 11/1987 | Wong |
| 4,711,251 A | 12/1987 | Stokes |
| 4,723,958 A | 2/1988 | Pope |
| 4,732,915 A | 3/1988 | Ayer |
| 4,751,071 A | 6/1988 | Magruder |
| 4,756,314 A | 7/1988 | Eckenhoff |
| 4,765,989 A | 8/1988 | Wong |
| 4,777,049 A | 10/1988 | Magruder |
| 4,783,337 A | 11/1988 | Wong |
| 4,783,413 A | 11/1988 | Suter |
| 4,837,111 A | 6/1989 | Deters |
| 4,851,228 A | 7/1989 | Zentner |
| 4,851,229 A | 7/1989 | Magruder |
| 4,865,845 A * | 9/1989 | Eckenhoff et al. ........... 424/424 |
| 4,880,631 A | 11/1989 | Haslam |
| 4,886,668 A | 12/1989 | Haslam |
| 4,898,582 A | 2/1990 | Faste |
| 4,968,507 A | 11/1990 | Zentner |
| 4,976,966 A | 12/1990 | Theeuwes |
| 5,030,216 A | 7/1991 | Theeuwes |
| 5,151,093 A | 9/1992 | Theeuwes |
| 5,169,390 A | 12/1992 | Athayde |
| 5,257,987 A | 11/1993 | Athayde |
| 5,273,752 A | 12/1993 | Ayer |
| 5,279,608 A | 1/1994 | Cherif Cheikh |
| 5,312,389 A | 5/1994 | Theeuwes |
| 5,318,540 A | 6/1994 | Athayde |
| 5,324,280 A | 6/1994 | Wong |
| 5,413,572 A | 5/1995 | Wong |
| 5,492,534 A | 2/1996 | Athayde |
| 5,562,654 A | 10/1996 | Smith |
| 5,607,696 A | 3/1997 | Rivera |
| 5,612,059 A | 3/1997 | Cardinal |
| 5,672,167 A | 9/1997 | Athayde |
| 5,698,220 A | 12/1997 | Cardinal |
| 5,728,396 A * | 3/1998 | Peery et al. ................. 424/422 |
| 5,795,591 A | 8/1998 | Lee |
| 5,798,119 A | 8/1998 | Herbig |
| 5,801,188 A | 9/1998 | Hassenbusch |
| 5,827,538 A | 10/1998 | Cussler |
| 5,869,096 A | 2/1999 | Barclay |
| 5,869,097 A | 2/1999 | Wong |
| 5,876,752 A | 3/1999 | Herbig |
| 5,904,934 A | 5/1999 | Maruyama |
| 5,980,509 A | 11/1999 | Magruder |
| 5,985,305 A | 11/1999 | Peery |
| 5,997,527 A | 12/1999 | Gumucio |
| 6,117,125 A * | 9/2000 | Rothbarth et al. .......... 604/523 |

OTHER PUBLICATIONS

Edith Mathiowitz; (Ed.), *Encyclopedia of Controlled Drug Delivery*, John Wiley & Sons vol. 2, pp. 896–920, 1999.

Tony Yaksh(Ed.), *Animal Models Of Intrathecal And Epidural Drug Delivery*, Ch. 13, Spinal Drug Delivery, Elsevier Science, pp. 317–344, 1999.

Tony Yaksh (Ed.), Mark Wallace, *Human Spinal Drug Delivery: Methods and Technology,*, Ch. 14, Spinal Drug Delivery, Elsevier Science, oo, 345–370, 1999.

Alzet Osmotic Pumps, *Reference from 1991–1998 On The Administration Of Opiods Using ALZET Osmotic Pumps (OPIO–Q4–99)*, pp. 1–13, World Wide Web, http://www.alzet.com/bibliography/bib_pages/opio.htm (Printed on Oct. 13, 2000).

* cited by examiner

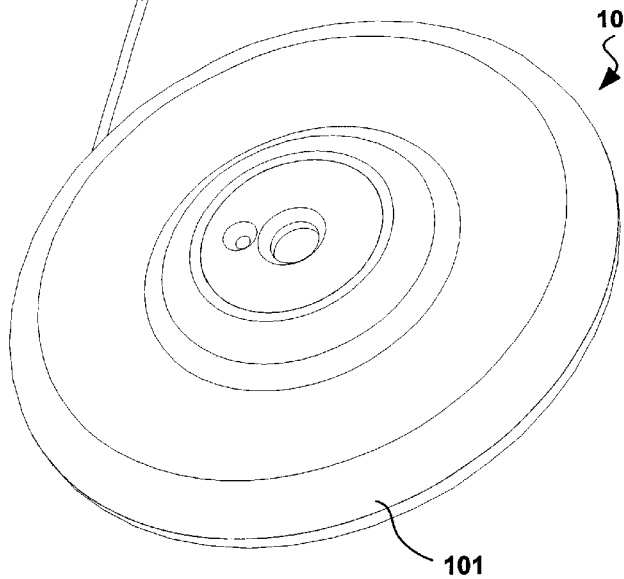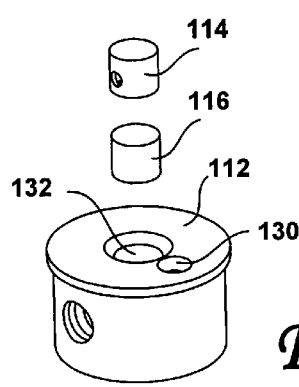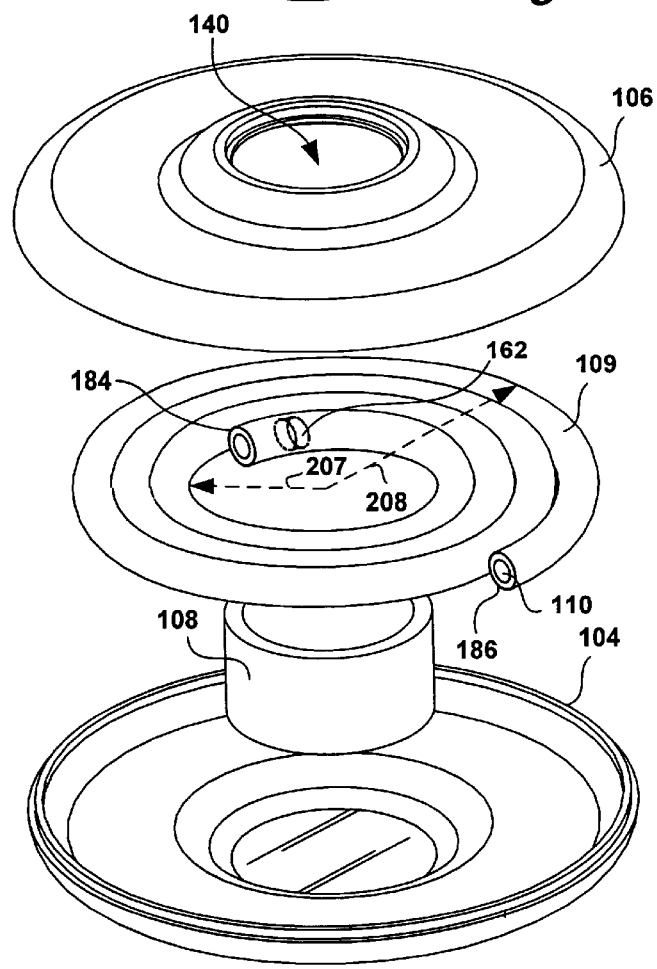

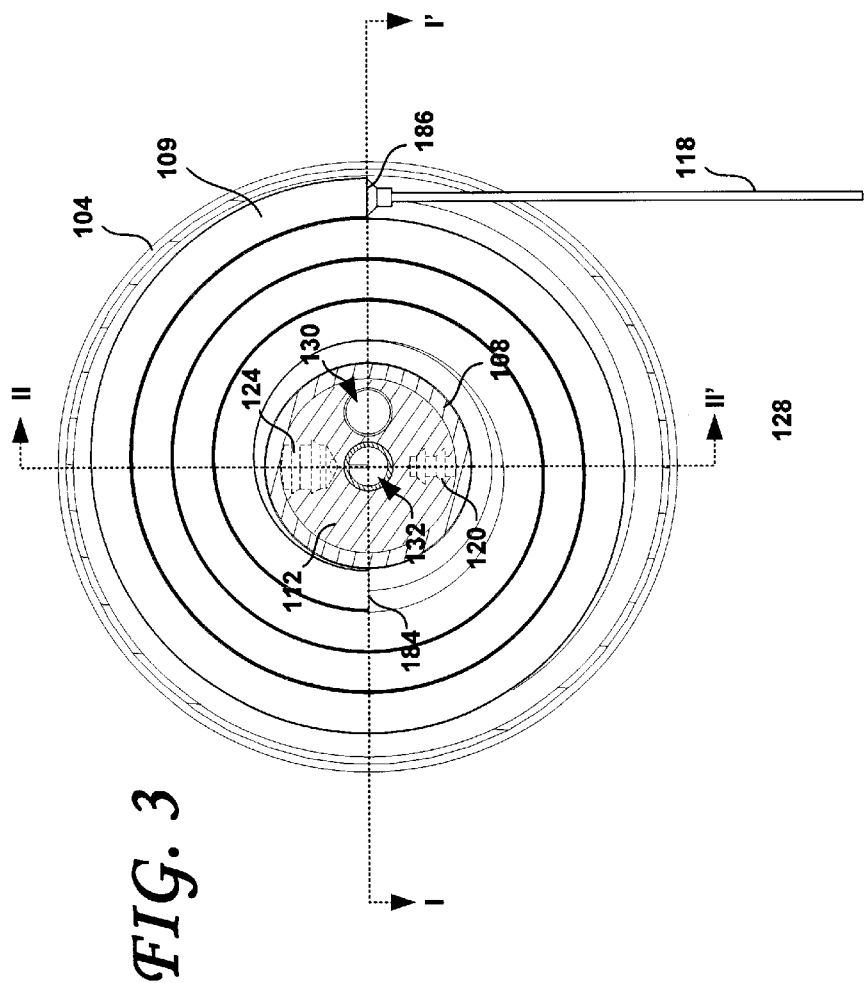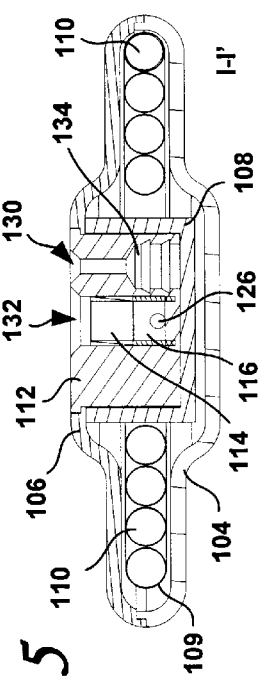

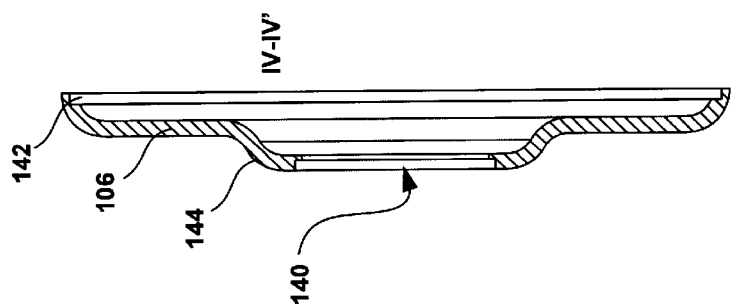
FIG. 10
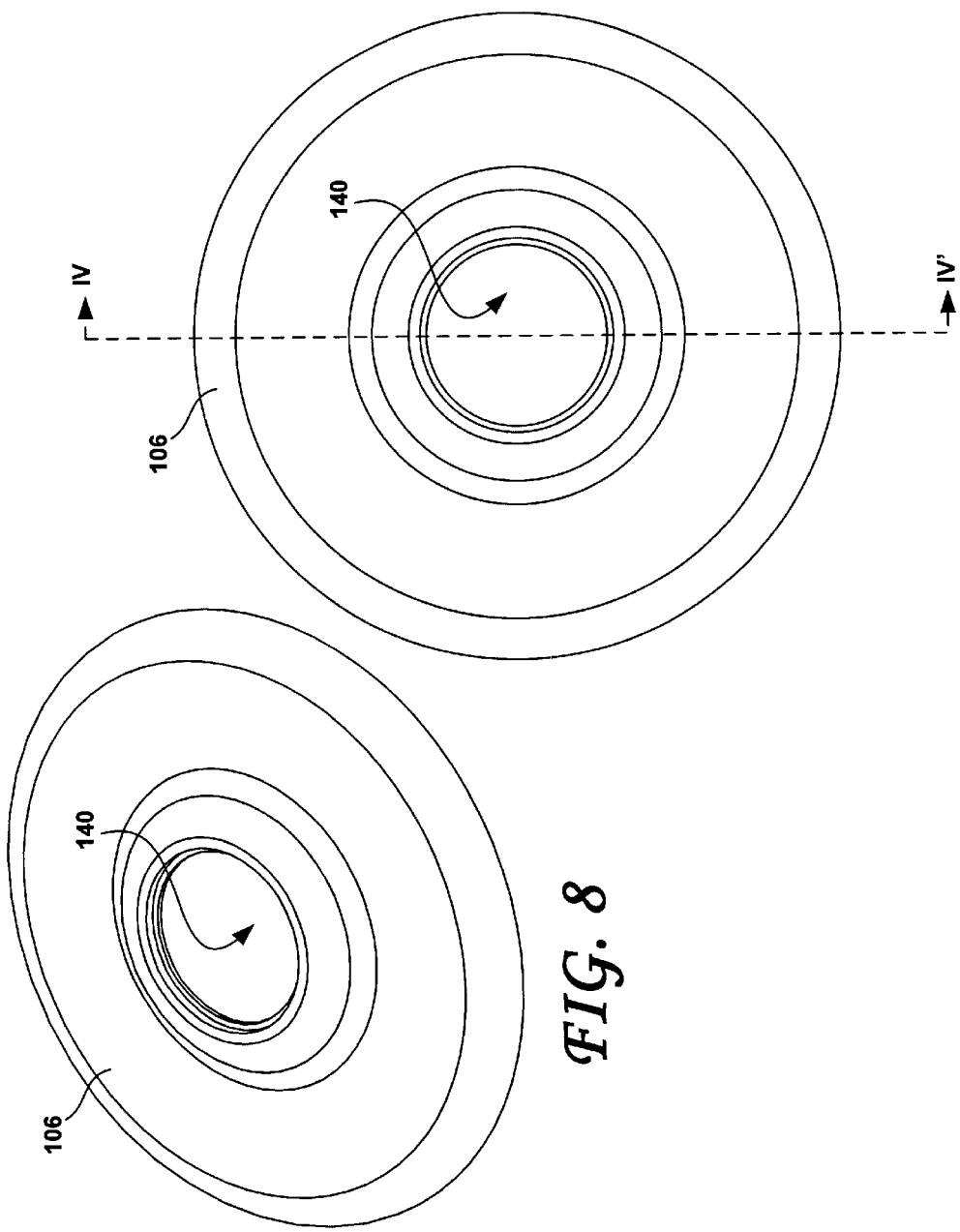
FIG. 9
FIG. 8

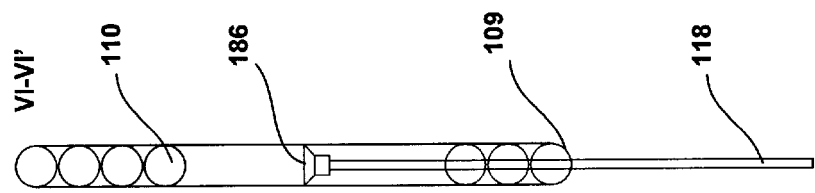
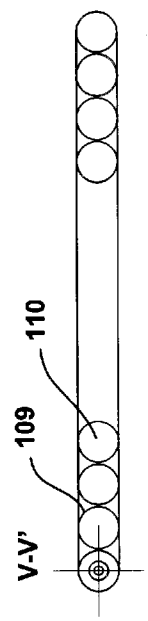
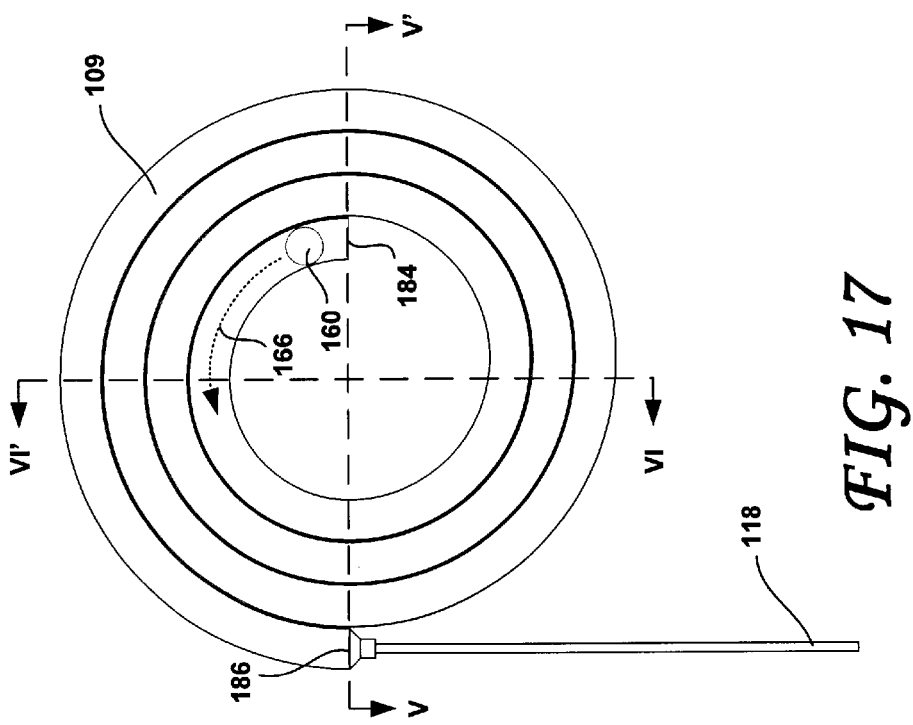

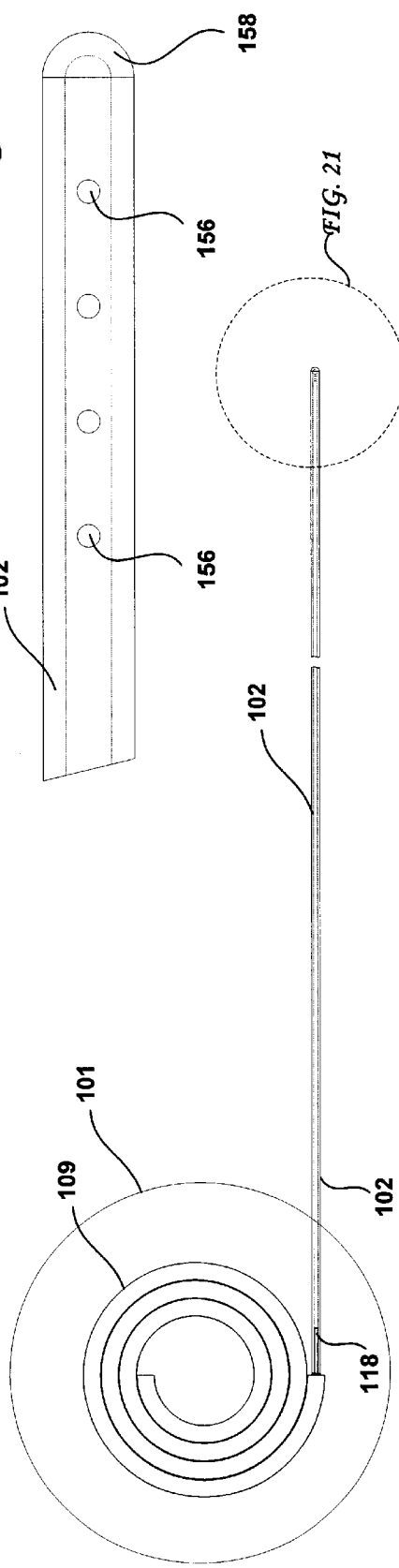
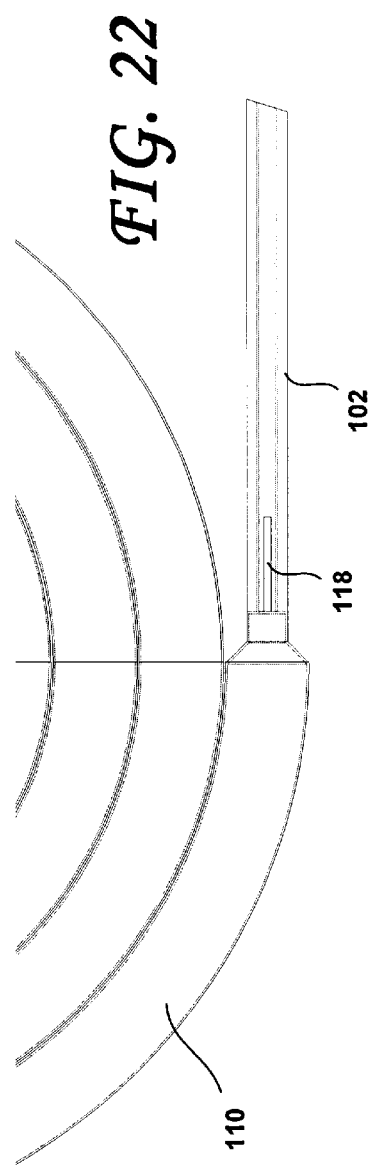

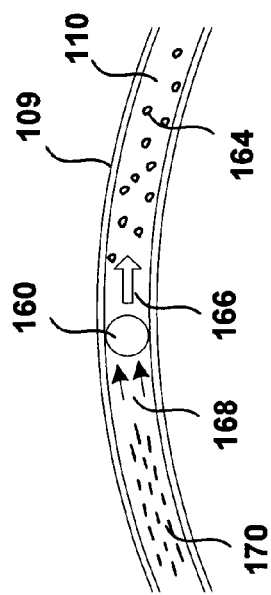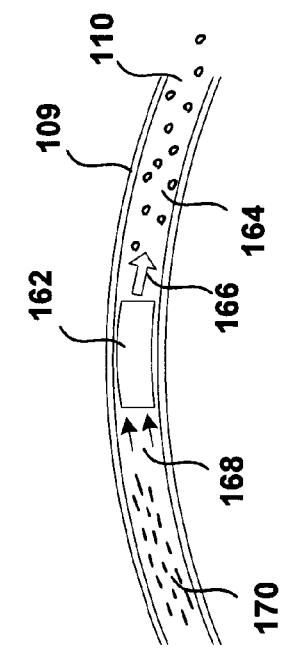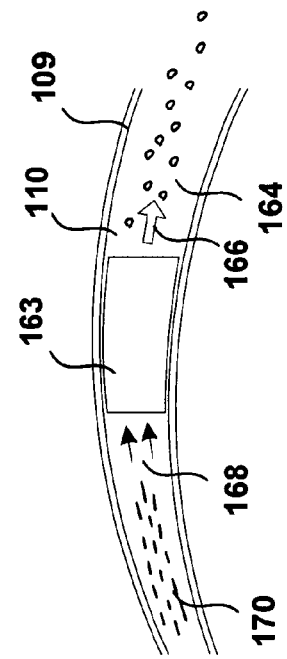

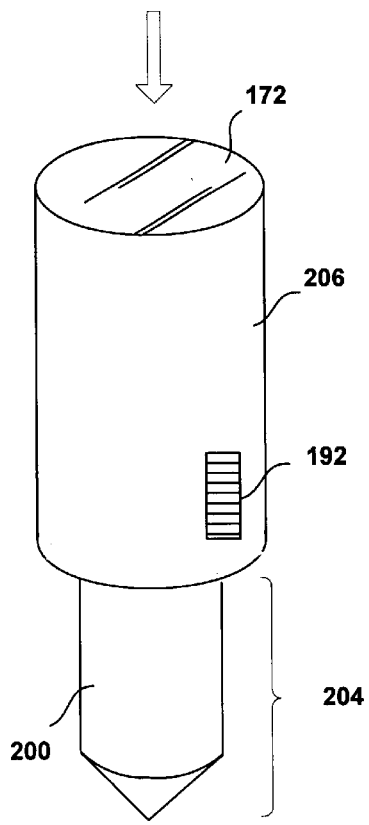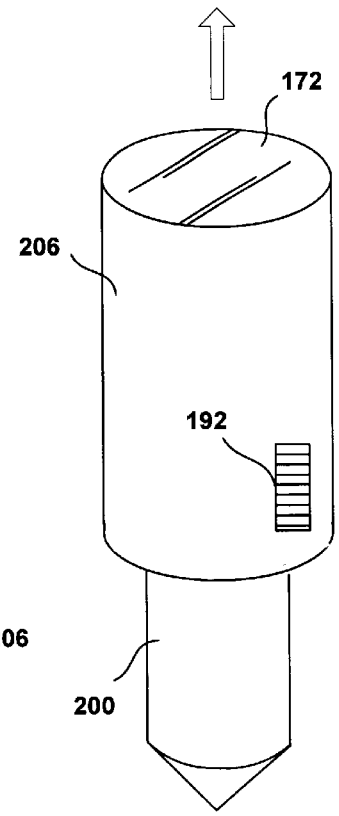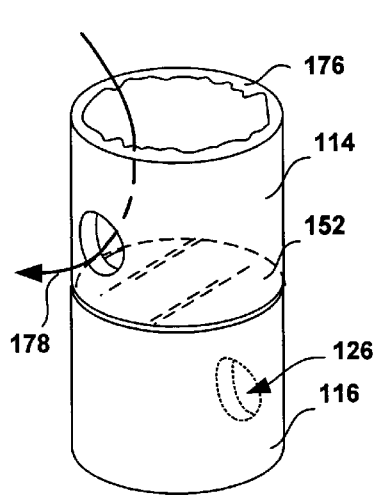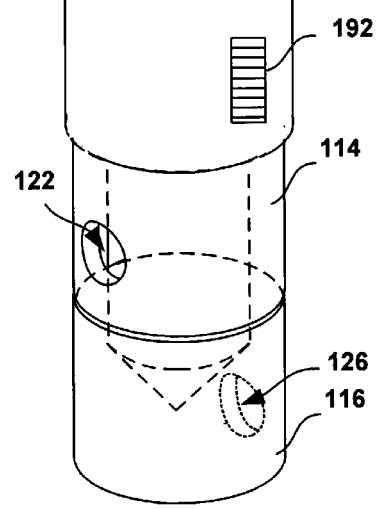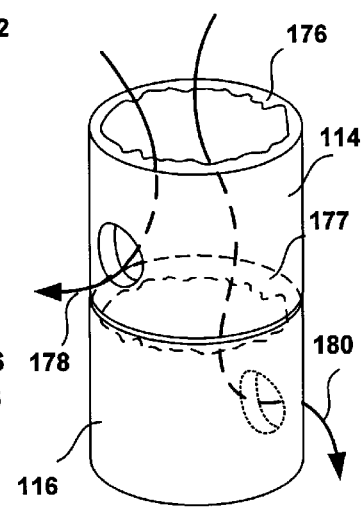
FIG. 29    FIG. 30    FIG. 31

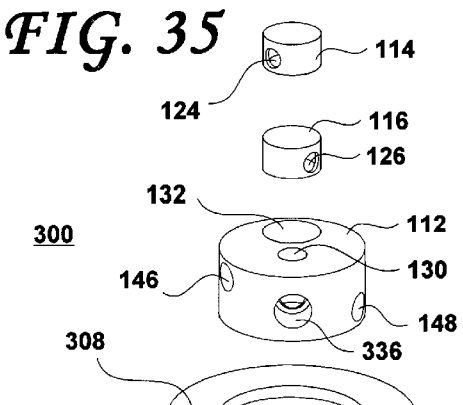
FIG. 35
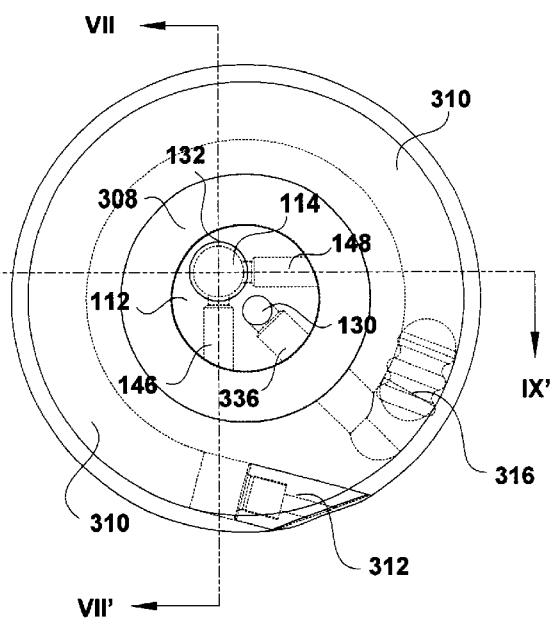
FIG. 36a
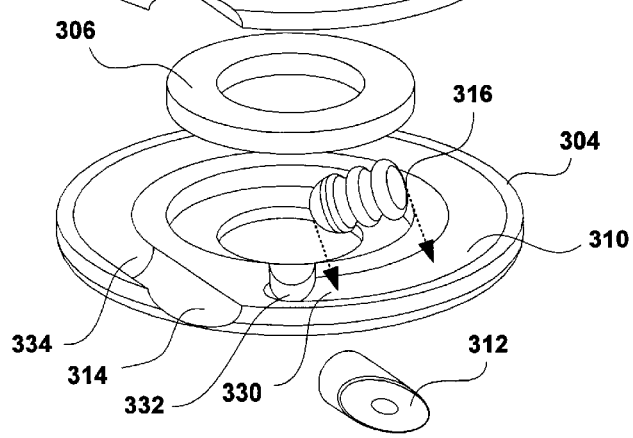
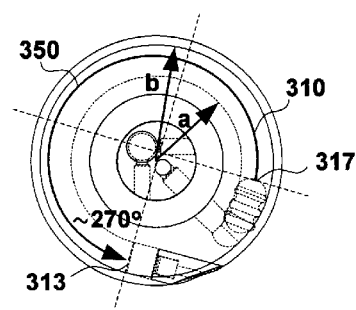
FIG. 36b
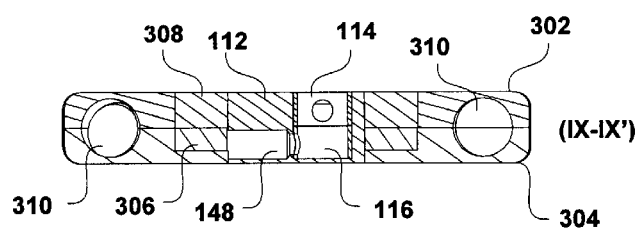
FIG. 37
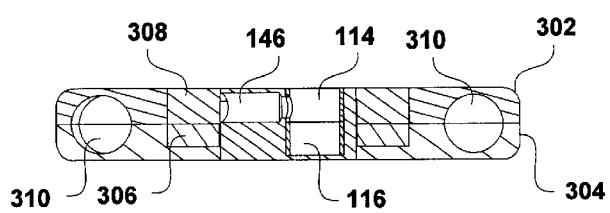
FIG. 38

IMPLANTABLE OSMOTIC PUMP

BACKGROUND OF THE INVENTION

1. Field of the Invention

The present invention relates generally to the field of drug delivery systems. In particular, the present invention relates to implantable osmotic pump systems.

2. Description of the Related Art

Since the beginning of modern medicine, drugs have been administered orally. Patients have taken pills as recommended by their physician. The pills must pass through the digestive system and then the liver before they reach their intended delivery site (e.g., the vascular system). The actions of the digestive tract and the liver typically reduce the efficacy of medication by about 33%. Furthermore, oral medications must be administered by the patient. Patient compliance to the prescribed delivery profile is often poor. Studies suggest that 40% of patients do not comply with their oral medication consumption instructions. This causes two concerns. First, patients who do not take their medication as instructed are not maintaining blood drug levels within the therapeutic window and are therefore not receiving adequate therapy for their disease. A second, worse scenario than receiving too little medication occurs when the patient may be taking too much medication either by accident or purposefully in order to make up for a missed dose. Both of these patient-controlled scenarios can be dangerous to the patient, and at a minimum may prolong or aggravate their disease. Subcutaneous drug delivery and intravenous drug delivery have the advantage of bypassing the acidic and enzymatic action of the digestive system. Unfortunately, IV administration requires the use of a percutaneous catheter or needle to deliver the drug to the vein. The percutaneous site requires extra cleanliness and maintenance to minimize the risk of infection.

Infection is such a significant risk that IV administration is often limited to a number of weeks, at most. In addition, the patient must wear an external pump connected to the percutaneous catheter if the therapy is intended to last longer than a few hours and the patient desires to be ambulatory. Subcutaneous drug delivery can be either partially implanted or totally implanted. Partially implanted systems rely on a percutaneous catheter or needle stick to deliver the medication, therefore, partially implanted systems have the same limitations as IV systems. Totally implanted systems have fewer maintenance requirements and are far less prone to infection than IV or partially implanted systems.

In the 1970s, a new approach toward sustained drug delivery was commercialized for animal use only. The driving force of such pumps was based upon a new approach utilizing the principle of osmosis. A recent example of such a pump is described listed in U.S. Pat. No. 5,728,396. This patent discloses an implantable osmotic pump that achieves a sustained delivery of leuprolide. The pump includes a right-cylindrical impermeable reservoir that is divided into a water-swellable agent chamber and a drug chamber, the two chambers being divided by a movable piston. Fluid from the body is imbibed through a semipermeable membrane into the water-swellable agent chamber. As the water-swellable agent in the water-swellable agent chamber expands in volume, it pushes on the movable piston, which correspondingly decreases the volume of the drug chamber and causes the drug to be released through a diffusion outlet at a substantially constant rate.

A limitation of the osmotic pump disclosed in the above-identified patent, however, is that its infusion rate cannot be adjusted once it is implanted. This is acceptable for medications that do not need rate adjustment, but often physicians desire to adjust the infusion rate based on the clinical status of the patient. One example of when a physician would want to increase the infusion rate is in the field of pain management. Osmotic pumps can be used to deliver medication to treat pain lasting over an extended period of time. Pain, however, often increases with time, and sometimes patients become tolerant to pain medications; therefore, more medication is needed to effectively treat the pain. The system disclosed in the above-identified patent does not allow a rate increase after implantation, so the physician must surgically remove the current implant and implant an additional pump to deliver the correct dosage. However, the prospect of yet another surgical procedure may cause many patients to forego the potential benefits of the larger dose and may also cause their physicians to advise against the initial procedure altogether.

The aspect ratio of such cylindrical osmotic pump delivery devices is large, and often not compatible with the human body. Indeed, the human body does not have naturally-formed right-cylindrical cavities in which to implant such devices in the patient, in an unobtrusive and comfortable manner.

What are needed, therefore, are improved osmotic pumps. What are also needed are improved implantable osmotic pumps that conform to the patient's anatomy and that more closely match the =topology of the implant site. Also needed are novel implantable osmotic pumps for long term delivery of a pharmaceutical agent that do not rely upon a right-cylindrical pharmaceutical agent compartment and/or conventional cylindrical pistons. Also needed are implantable pumps that enable the physician to increase the dose of pharmaceutical agent delivered to the patient without, however, removing the pump from the implant site.

SUMMARY OF THE INVENTION

It is an object of the present invention, therefore, to provide improved pumps. Another object of the present invention is to provide improved implantable osmotic pumps that conform to the patient's anatomy and that more closely match the topology of the implant site. A still further object is to provide novel implantable osmotic pumps for long term delivery of a pharmaceutical agent that do not rely upon a right-cylindrical pharmaceutical agent compartment and/or conventional cylindrical pistons. Preferably, such improved pumps should enable the physician to increase the dose of pharmaceutical agent delivered to the patient without removing the pump from the implant site.

In accordance with the above-described objects and those that will be mentioned and will become apparent below, an implantable osmotic pump for delivering a pharmaceutical agent to a patient, according to an embodiment of the present invention, includes an osmotic engine; a substantially toroidal compartment adapted to store a pharmaceutical agent, and a piston disposed within the compartment, the osmotic engine being configured to cause the piston to travel within the compartment and deliver the pharmaceutical agent when the pump is implanted in the patient.

The pump may include a tube coiled at least partially around the osmotic engine, an inner lumen of the tube defining the pharmaceutical agent compartment. The tube may include or be formed of metals, polymers and/or polyimid, for example. The compartment may be disposed at least partially around the osmotic engine. The tube may be rigid and the osmotic engine may be disposed within the tube.

According to other embodiments, the osmotic engine may include a base, a cylindrical wall attached to the base and a free end opposite the base. The pump may include a housing configured to enclose at least the osmotic engine and the tube. The housing may include a first housing half and a second housing half that mates with the first housing half. Each of the first and second housing halves may define a saucer shape, for example. Each of the first and the second housing halves may be substantially circular in shape. The first housing half may define a substantially circular opening. The pump may further include a membrane enclosure, the membrane enclosure being partially surrounded by the osmotic engine and including an initial dose semipermeable membrane that is configured to allow water from the patient to reach the osmotic engine when the pump is implanted. The pump may be configured to deliver an initial dose of the pharmaceutical agent to the patient at a selected initial infusion rate, the selected initial infusion rate being related to a thickness, a composition and/or a surface area of the initial dose semipermeable membrane. The initial dose semipermeable membrane may be fitted with an initial dose impermeable membrane that initially seals the initial dose semipermeable membrane.

A dose escalation assembly may be fitted in the membrane enclosure, the dose escalation assembly being adapted to selectively increase an amount of water from the patient that reaches the osmotic engine when the pump is implanted. The dose escalation assembly may include a first impermeable membrane configured to enable water from the patient to reach the osmotic engine through a first fluid path only after being breached. The dose escalation assembly may include a first impermeable membrane configured to enable water from the patient to reach the osmotic engine through a first fluid path only after being breached, and a second impermeable membrane configured to enable water from the patient to reach the osmotic engine through a second fluid path only after being breached, the first path being distinct from the second path. The first and second impermeable membranes may be disposed in the membrane enclosure in a stacked configuration wherein the first impermeable membrane must be breached before the second impermeable membrane can be breached. The first fluid path may include a first semipermeable membrane and the second fluid path may include a second semipermeable membrane that is distinct from the first semipermeable membrane. The pump may be configured to deliver a first dose of the pharmaceutical agent to the patient at a selected first infusion rate and a second dose of the pharmaceutical agent to the patient at a selected second infusion rate that is greater than the first infusion rate, the selected first and second infusion rates being related to a thickness, a composition and/or a surface area of the first and second semipermeable membranes, respectively.

The osmotic engine may include a hygroscopic salt and/or an absorbent polymer. The absorbent polymer may include a material selected from a group including poly(acrylic acid), potassium salt; poly(acrylic acid), sodium salt; poly(acrylic acid-co-acrylamide), potassium salt; poly(acrylic acid), sodium salt-graft-poly(ethylene oxide); poly(2-hydroxethyl methacrylate); poly(2-hydroxypropyl methacrylate) and poly(isobutylene-co-maleic acid) or derivatives thereof.

The tube-shaped compartment may have a substantially constant inner diameter over a length thereof. Alternatively, the tube-shaped compartment may have a non-constant inner diameter over a length thereof. The tube may be coiled at least twice around the osmotic engine. A layer of epoxy may encase at least the tube. The tube may include polyimid, for example. The tube may define a proximal end adjacent the osmotic engine and a distal end at an end opposite the proximal end, and the pump may further include a catheter coupled to the distal end. The catheter may include a radiopaque tip. The piston may include a sphere, an elastomeric cylinder and/or an elastomeric conical section and may include stainless steel, a refractory metal, plastic, nylon and/or rubber, for example.

The tube-shaped compartment may be pre-loaded with a volume of the pharmaceutical agent. For example, the pharmaceutical agent may be therapeutically effective for pain therapy, hormone therapy, gene therapy, angiogenic therapy, anti-tumor therapy, chemotherapy, allergy therapy, hypertension therapy, antibiotic therapy, bronchodilation therapy, asthmatic therapy, arrhythmia therapy, nootropic therapy, cytostatic and metastasis inhibition therapy, migraine therapy, gastrointestinal therapy and/or other pharmaceutical therapies.

The dose escalation assembly may include a first saturated saline solution between the first impermeable membrane and the first semipermeable membrane, and a second saturated saline solution between the second impermeable membrane and the second semipermeable membrane.

The present invention is also a kit, comprising an implantable osmotic pump for delivering a pharmaceutical agent to a patient, including an osmotic engine, a tube coiled around the osmotic engine, the tube defining an inner tube-shaped compartment adapted to store a pharmaceutical agent, and a piston disposed within the tube-shaped compartment, the osmotic engine being configured to exert a force on the piston to cause the piston to travel within the tube-shaped compartment and deliver the pharmaceutical agent when the pump is implanted in the patient, and a catheter configured to attach to the pump. The pump may further include a membrane enclosure, the membrane enclosure being partially surrounded by the osmotic engine and an initial dose semipermeable membrane that is configured to allow water from the patient to reach the osmotic engine when the pump is implanted. The pump may further include a dose escalation assembly fitted in the membrane enclosure, the dose escalation assembly being adapted to selectively increase an amount of water from the patient that reaches the osmotic engine when the pump is implanted. The dose escalation assembly may include a first impermeable membrane configured to enable water from the patient to reach the osmotic engine through a first fluid path only after being breached, and a second impermeable membrane configured to enable water from the patient to reach the osmotic engine through a second fluid path only after being breached, the first path being distinct from the second path. The kit may further include a dose escalation pen configured to breach the first and/or second impermeable membranes. The dose escalation pen may include a dose selection actuator that is adapted to re-configure the dose escalation pen to selectively breach one of the first and second impermeable membranes. The tube-shaped compartment may be pre-loaded with the pharmaceutical agent.

The present invention is also a method of delivering a pharmaceutical agent to a patient, comprising steps of implanting a pump into the patient, the pump including a pump engine and a compartment adapted to store a pharmaceutical agent, the compartment defining at least a partial torus around the osmotic engine, and causing a piston to travel a distance within the compartment and to deliver a dose of pharmaceutical agent corresponding to the distance traveled out of the compartment. The implanting step may implant the pump (and/or portions thereof) intravascularly, subcutaneously, epidurally, intrathecally and/or intraventricularly, for example. A step of selectively increasing the dose in a stepwise manner over a treatment period without removing the pump from the patient may also be carried out. The pump engine may include an osmotic engine and the pump may include an initial dose semipermeable membrane initially exposed to the patient and at least one second semipermeable membrane initially not exposed to the patient. The increasing step may then include a step of selectively exposing the at least one second semipermeable membrane to the patient. The pump the engine may include an osmotic engine in fluid communication with the piston and the causing step may include a step of increasing a volume of the osmotic engine.

The present invention is also a pump, comprising a pump engine; a tube coiled around the engine, the tube defining an inner tube-shaped compartment adapted to store a fluid, and a piston disposed within the tube-shaped compartment, the engine being adapted to cause the piston to travel within the tube-shaped compartment and to force a dose of the fluid out of the pump. The pump engine may include an osmotic engine. The fluid may include a pharmaceutical agent. A catheter may be coupled to the tube. The pump may be fully implantable in a body and the pump engine and the tube may be enclosed in a biocompatible pump housing. The pump may include a dose escalation assembly, the escalation assembly being configured to selectively increase the dose of fluid delivered. The dose escalation assembly may comprise means for increasing the dose delivered in a stepwise manner. The piston may include a sphere, an elastomeric cylinder and/or an elastomeric conical section, for example.

According to another embodiment thereof, the present invention is an osmotic pump, comprising an osmotic engine and a pump housing enclosing the osmotic engine and defining a substantially toroidal space adapted to contain a volume of pharmaceutical agent. The pump housing may define a substantially circular outline. The substantially toroidal space may define an inner and an outer radius, and the osmotic engine may be disposed within the inner radius. The pump may include a tube disposed within the toroidal space, the tube defining an inner lumen adapted to contain the volume of pharmaceutical agent. Alternatively, the pump housing may include a first housing half and a second housing half, the first and second housing halves defining, when mated together, the substantially toroidal space, the substantially toroidal space being fluid tight. The pump may further include a semipermeable membrane enclosure and a semipermeable membrane fitted within the semipermeable membrane enclosure. A single semipermeable membrane may be fitted within the semipermeable membrane enclosure, in which case, the pump is a single stage pump. Alternatively, the pump may be an n-stage pump and the semipermeable membrane enclosure may be fitted with n semipermeable membranes, each of the n stages being configured to be selectively activated after implantation of the pump. The pump may also include an OFF switch mechanism configured to be selectively activated after implantation of the pump. The pump may also include a filter assembly to filter the pharmaceutical agent. The filter assembly may include a plug of porous material, the porous material defining pores selected to have an average size of between about 2 microns and about 80 microns. For example, the filter assembly may include a plug of porous material, the porous material being hydrophilic or hydrophobic (or having hydrophilic or hydrophobic characteristics).

The present invention is also an implantable osmotic pump, comprising a semipermeable membrane; a housing adapted to enclose a volume of pharmaceutical agent and a portion of the semipermeable membrane; an osmotic engine adapted to cause the pharmaceutical agent to be delivered out of the pump as an osmotic pressure differential develops across the semipermeable membrane, and an OFF switch, the OFF switch being effective to reduce the osmotic pressure differential across the semipermeable membrane substantially to zero, and/or an ON switch, the ON switch being effective to enable the pump to begin to deliver the pharmaceutical agent out of the pump. The OFF switch may include an OFF switch impermeable membrane and the OFF switch may be configured to turn the pump OFF (reduce the osmotic pressure substantially to zero) only when the OFF switch impermeable membrane is breached. The OFF switch may define a lumen adapted to allow fluid to bypass the semipermeable membrane when the OFF switch impermeable membrane is breached. The ON switch may include an impermeable membrane disposed over the semipermeable membrane, the pump being turned ON (adapted to begin delivery of the pharmaceutical agent) only after the impermeable membrane is breached. A volume of saturated saline solution may be disposed between the semipermeable membrane and the impermeable membrane.

The pharmaceutical agent compartment of the pump may contain Sufentanil, for example, and/or may contain other medications. The sufentanil may be at a concentration of up to about 500,000 $\mu$g/mL. The pharmaceutical agent may include Sufentanil and the pump may be configured for a daily delivery rate of Sufentanil of up to about 25 micrograms per day when the pump is configured to be implanted intraventricularly; a daily delivery rate of Sufentanil of up to about 50 micrograms per day when the pump is configured to be implanted intrathecally; a daily delivery rate of Sufentanil of up to about 500 micrograms per day when the pump is configured to be implanted epidurally; a daily delivery rate of Sufentanil of up to about 1500 micrograms per day when the pump is configured to be implanted subcutaneously, and a daily delivery rate of Sufentanil of up to about 1500 micrograms per day when the pump is configured to be implanted intravascularly. The catheter and the pump may be dimensioned to infuse a dose of pharmaceutical agent of up to about 1500 $\mu$g/day over a treatment period, for example.

According to another embodiment thereof, the present invention is also a filter assembly for an osmotic pump, the filter defining a first end configured to mate with the osmotic pump a second end configured to be exposed, in use, to an aqueous environment and including a filter between the first and second ends. The filter may include a porous material, the porous material defining pores selected to have an average size of between about 2 microns and about 80 microns. The plug of porous material may be hydrophilic or hydrophobic (or have hydrophobic or hydrophilic properties).

BRIEF DESCRIPTION OF THE DRAWINGS

For a further understanding of the objects and advantages of the present invention, reference should be made to the following detailed description, taken in conjunction with the accompanying figures, in which:

FIG. 1 is a perspective view of the osmotic pump according to an embodiment of the present invention.

FIG. 2 is an exploded view of the osmotic pump according to an embodiment of the present invention, showing the major components thereof.

FIG. 3 is a plan view of the osmotic pump according to an embodiment of the present invention in which the first half of the housing has been removed.

FIG. 4 is a cross sectional view of the osmotic pump of FIG. 3, taken along lines II—II'.

FIG. 5 is a cross sectional view of the osmotic pump of FIG. 3, taken along lines I—I'.

FIG. 8 is a perspective view of the first half of the osmotic pump housing according to an embodiment of the present invention.

FIG. 9 is a plan view of the first half of the osmotic pump housing of FIG. 8.

FIG. 10 is a cross-sectional view of the first half of the osmotic pump housing of FIG. 9, taken along lines IV—IV'.

FIG. 17 is a plan view of the coiled tube, according to an embodiment of the present invention.

FIG. 18 is a cross-sectional view of the tube of FIG. 17, taken along line V—V'.

FIG. 19 is a cross-sectional view of the coiled tube of FIG. 17, taken along line VI—VI'.

FIG. 20 illustrates the tube coupled to a catheter, according to an embodiment of the present invention.

FIG. 21 illustrates the distal tip of the catheter of FIG. 20, according to an embodiment of the present invention.

FIG. 22 illustrates the proximal end of the catheter of FIG. 20, according to an embodiment of the present invention.

FIG. 23 shows a n embodiment of a piston within the coiled pharmaceutical agent compartment, according to an embodiment of the present invention.

FIG. 24 shows a further embodiment of a piston within the coiled pharmaceutical agent compartment, according to an embodiment of the present invention.

FIG. 25 shows a further embodiment of still another piston within the coiled pharmaceutical agent compartment, according to an embodiment of the present invention.

FIG. 29 shows a fourth step of a method by which the impermeable membrane of the second impermeable membrane can may be breached so as to further escalate a dose of pharmaceutical agent delivered to the patient, according to an embodiment of the present invention.

FIG. 30 shows a fifth step of a method by which the impermeable membrane of the second impermeable membrane can may be breached so as to further escalate a dose of pharmaceutical agent delivered to the patient, according to an embodiment of the present invention.

FIG. 31 shows a sixth step of a method by which the impermeable membrane of the second impermeable membrane can may be breached so as to further escalate a dose of pharmaceutical agent delivered to the patient, according to an embodiment of the present invention.

FIG. 35 is an exploded view of a three-stage osmotic pump, according to another embodiment of the present invention.

FIG. 36a is a top view of a three stage osmotic pump according to the present invention, showing the internal structure thereof in dashed lines.

FIG. 36b is a reduced-size (relative to FIG. 36a) top view of a three stage osmotic pump, showing selected exemplary dimensions thereof.

FIG. 37 is a cross-sectional view of a three stage osmotic pump according to the present invention, taken along cross-sectional line IX—IX' of FIG. 36.

FIG. 38 is a cross-sectional view of a three stage osmotic pump according to the present invention, taken along cross-sectional line VII—VII' of FIG. 36.

DESCRIPTION OF THE INVENTION

Figure 7:
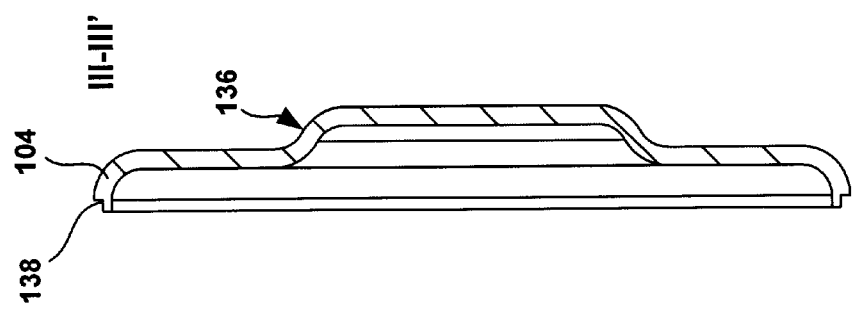
FIG. 7 is a cross sectional view of the second half of the osmotic pump housing, taken along lines III—III'.

FIG. 1 is a perspective view and FIG. 2 shows an exploded view of the pump 100 according to an embodiment of the present invention. Considering FIGS. 1 and 2 collectively, the pump 100 includes a pump engine 108 and a substantially toroidal compartment around the engine 108. The toroidal compartment is bounded by an inner radius 207 and an outer radius 208 and is adapted to contain a fluid, such as a pharmaceutical agent. According to an embodiment of the present invention, the pharmaceutical agent compartment is tube-shaped and is defined by an inner lumen 110 of a tube 109 that may be coiled at least partially around the osmotic engine 108. The tube 109 has a proximal end 184 and a distal end 186. The tube 109 may include or be formed of, for example, polyimid. A piston 162 is disposed in the tube-shaped compartment 110. The piston is adapted to travel (in the direction from the proximal end 184 to the distal end 186 of the tube 109) within the tube-shaped compartment 110 and to cause a volume of fluid to be forced out of the distal end 186 of the tube 109. As shown in FIG. 1, a catheter 102 may be coupled to the distal end 186 of the tube 109, to enable the fluid forced out the distal end 186 of the tube 109 to be delivered to the intended delivery site within the patient. In one embodiment of the present invention, the pump engine 108 includes an osmotic engine. The pump 100 may further include a pump housing 101 that is configured to enclose (at least) the pump engine 108 and the tube 109. As shown in FIG. 2, the pump housing 101 may include a first housing half 106 and a mating second housing half 104. According to an embodiment of the present invention, the first and second pump housing halves 106, 104 mate to one another like a clamshell, in a fluid-tight fashion. As shown, the first and second housing halves 106, 104 may each have a generally circular outline (as may the entire pump 100) and have a generally define a saucer shape. The first housing half 106 may further define an opening 140, which may be circular in shape.

Figure 16:
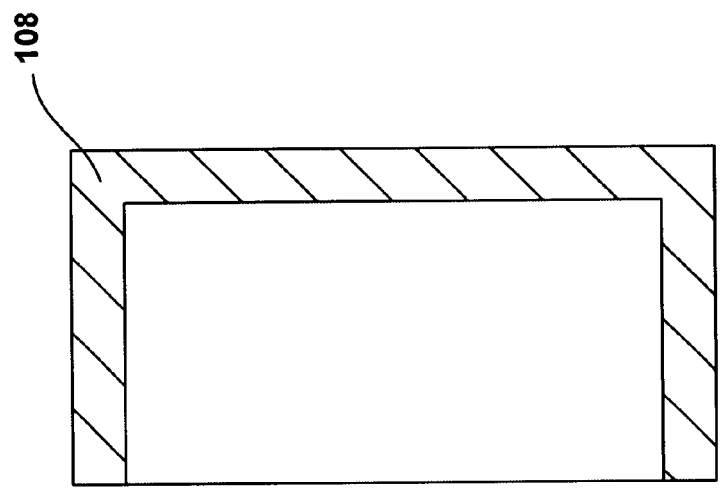
FIG. 16 is a side view of the osmotic engine of FIG. 15.
Figure 15:
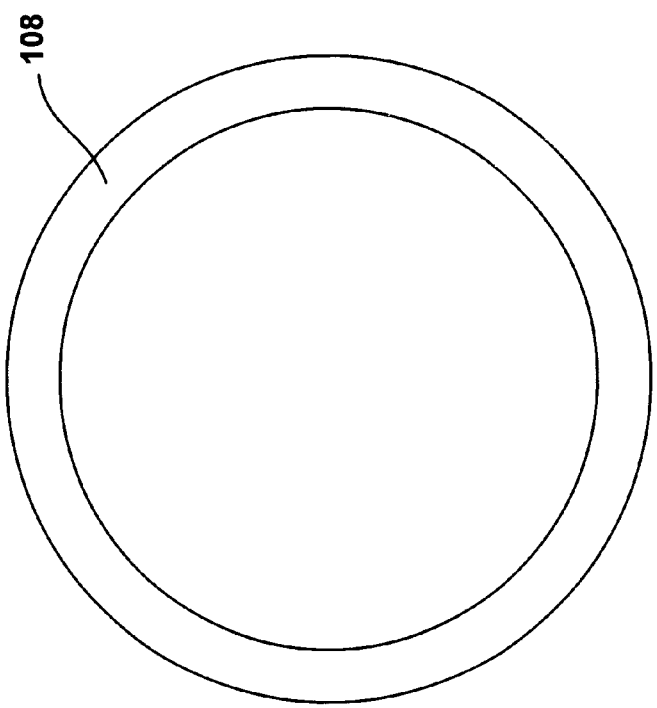
FIG. 15 is a plan view of the osmotic engine of the osmotic pump, according to an embodiment of the present invention.

The present invention will now be described in terms of an implantable osmotic pump for delivering a pharmaceutical agent to a patient, although the present invention is not so limited. The pump and/or the catheter 102 may be implanted intravascularly, subcutaneously, epidurally, intrathecally and/or intraventricularly, for example. As shown in FIG. 2 as well as in FIGS. 15 and 16, the pump engine 108 (referred to hereafter as osmotic engine 108, although the present invention is not limited to osmotic-type pump engines) may be shaped like hollow, open-ended right cylinder. The osmotic engine 108 is hygroscopic and may include a salt block or a "salt wafer" and/or may include an absorbent polymer, such as poly(acrylic acid), potassium salt; poly(acrylic acid), sodium salt; poly(acrylic acid-co-acrylamide), potassium salt; poly(acrylic acid), sodium salt-graft-poly(ethylene oxide); poly (2-hydroxethyl methacrylate) and/or poly(2-hydroxypropyl methacrylate) and poly(isobutylene-co-maleic acid). Suitable absorbent polymers are available from Aldrich, Inc. of Milwaukee, Wis., for example. The osmotic engine 108 may include a base that may be disposed in a correspondingly shaped depression defined in the second housing half 104 and a cylindrical wall attached to the base.

According to an embodiment of the present invention, the pump 100 may include a generally cylindrical-shaped membrane enclosure 112. The membrane enclosure 112 may be fitted within and partially surrounded by the pump engine 108. The membrane enclosure 112 is dimensioned to closely fit the opening 140 defined in the first housing half 106. The membrane enclosure 112 may include an initial dose semipermeable membrane (formed of or including cellulose acetate, for example), as shown in FIG. 5, to create a fluid path for water through the initial water access port 130 defined in the membrane enclosure 112 to the osmotic engine 108. The initial water access port 130 may be spanned by a thin impermeable membrane 182, thereby defining an interstitial space between the initial dose semipermeable membrane and the impermeable membrane. This interstitial space may be filled with a saturated saline solution, to keep the initial dose semipermeable membrane fully hydrated prior to implantation of the pump 100 in a patient (not shown). Prior to implantation, the physician may breach the impermeable membrane 182 spanning the initial water access port 130 to allow water from the patient to enter the initial dose semipermeable membrane well 150 (see FIG. 12) and migrate across the initial dose semipermeable membrane 134 (see FIG. 5) to reach the osmotic engine 108. In this manner, the initial water access port 130, the thin impermeable membrane 182 and the saturated saline solution effectively form a pump ON switch. Indeed, after implantation of the pump but before breaching the thin impermeable membrane 182, the pump 100 does not deliver any pharmaceutical agent to the patient. It is only after breaching the thin impermeable membrane 182 that the pump becomes effective to initiate delivery of the contained pharmaceutical agent to the patient. The saturated saline solution between the impermeable membrane 182 and the underlying initial dose semipermeable membrane 150 insures that the onset of delivery of the pharmaceutical agent is not delayed by the time required for the initial dose semipermeable membrane 150 to hydrate.

The membrane enclosure 112 may also define a primary water access port 132 that may be (but need not be) concentric with the circumference of the membrane enclosure 112. A dose escalation assembly may fit within the primary water access port 132. The dose escalation assembly, according to the present invention, is adapted to selectively increase the amount of water from implantation site within the patient that reaches the osmotic engine 108. The dose escalation assembly may include one or more impermeable membrane cans fitted within the primary water access port 132 of the membrane enclosure 112. In the embodiment of FIG. 2, the dose escalation includes a first impermeable membrane can 114 stacked upon a second impermeable membrane can 116 whose structure and function is described hereunder.

Reference is now made to FIGS. 3–5, in which FIG. 3 is a plan view of the osmotic pump according to an embodiment of the present invention in which the first half of the housing has been removed, FIG. 4 is a cross sectional view of the osmotic pump of FIG. 3, taken along lines II—II' of FIG. 3 and FIG. 5 is a cross sectional view of the osmotic pump of FIG. 3, taken along lines I—I'.

FIG. 3 shows the tube 109 coiled around the osmotic engine 108 from the proximal end 184 to the distal end thereof, shown at 186. The distal end 186 of the coiled tube 109 may be fitted with a catheter ID tube 118 that facilitates the coupling of the catheter 102 to the distal end 186 of the tube 109. As shown in FIG. 5, the initial water access port 130 may lead to an initial dose semipermeable membrane 134 within the membrane enclosure 112. The membrane enclosure 112 is configured to enable water from the patient to flow into the initial water access port 130, to migrate across the initial dose semipermeable membrane 134 to reach the osmotic engine 108. As the water reaches the osmotic engine 108, the engine 108 swells in volume and increases the osmotic pressure differential across the initial dose semipermeable membrane 134 and pushes the piston 160 within the tube-shaped compartment defined by the tube 109 toward the distal end 186 thereof, as the expansion of the osmotic engine 108 is constrained to within the tube-shaped compartment 110. In so doing, the piston 160 displaces a volume of pharmaceutical agent within the tube-shaped compartment 110, which displaced volume of pharmaceutical agent is delivered out of the distal end 186 of the tube 109. The pharmaceutical agent is delivered at a selected initial infusion rate that is related to the thickness, composition and surface area of the initial dose semipermeable membrane 134. In the case wherein the initial dose semipermeable membrane 134 is implanted in a fully hydrated state, the pharmaceutical agent within the tube-shaped compartment is quickly delivered to the patient at the selected initial infusion rate. If the initial dose semipermeable membrane 134 is not pre-hydrated, the delivery of the pharmaceutical agent may be delayed until the membrane 134 becomes at least partially hydrated from water from the patient implant site. Until at least the first impermeable membrane cans 114 is breached, the only water that reaches the osmotic engine 108 enters the pump 100 through the initial water access port 130 to cross the initial dose semipermeable membrane 134.

Figure 14:
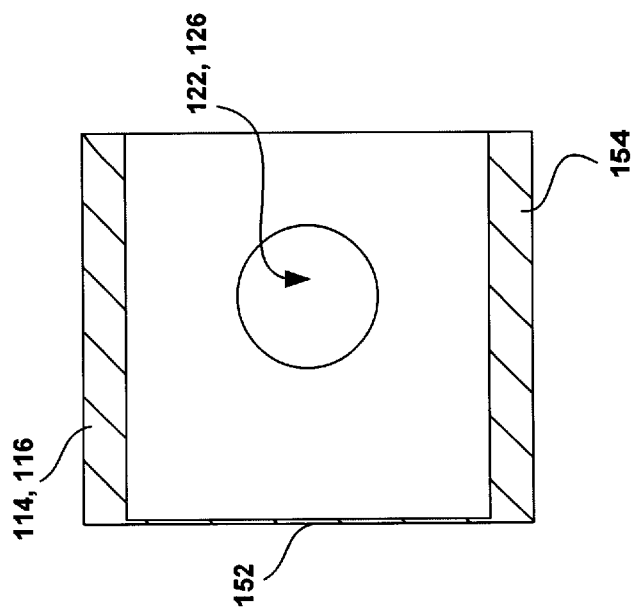
FIG. 14 shows a side view of the impermeable membrane can of FIG. 13.
Figure 13:
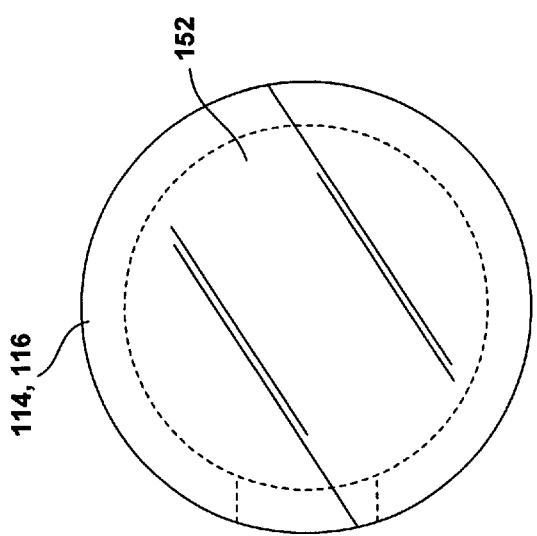
FIG. 13 is a plan view of an impermeable membrane can of an osmotic pump according to an embodiment of the present invention, showing the internal surface and through bore thereof in dashed lines.

As shown in FIG. 4, the membrane assembly 112 includes a first semipermeable membrane 120 and a second semipermeable membrane 124. The diameter of the semipermeable membranes 120, 124 is directly proportional to the flow rate of the pump of the present invention. As shown, the first semipermeable membrane 120 may be (but need not be) vertically offset from the second semipermeable membrane 124 in the membrane enclosure 112. Reference is now made to FIGS. 13 and 14, of which FIG. 13 is a plan view of an impermeable membrane can 114, 116 and of which FIG. 14 is a side view of the impermeable membrane can 114, 116 of FIG. 13. As shown therein, the cans 114, 116 include a cylindrical sidewall 154 and a through bore defined therein. Specifically, the sidewall of the first impermeable membrane can 114 defines a first through bore 122 and the sidewall of the second impermeable membrane can 116 defines a second through bore 126. An impermeable membrane 152 (shown in FIGS. 13 and 14 in its intact state) spans one of the free ends of each of the cans 114, 116. The impermeable membranes 152, according to the present invention, are impermeable at least to water from the patient implant site and are configured to be easily breached by the physician, as is detailed below. The impermeable membranes 152 may include or be formed of most any water impermeable material that is biologically inert, such as titanium and/or stainless steel, coated platinum or platinum-iridium for radiopacity, for example. The impermeable membranes 152 of the first and second cans 114, 116 may be surface ground to a thickness of about 1 or 2 thousandths of an inch, for example. The impermeable membranes 152 may alternatively include polyethylene, PET, PETG or PETE, for example. Preferably, the impermeable membranes 152 are radiopaque, so as to be visible under fluoroscopy, once the pump 100 is implanted. For example, a layer of radiopaque material may be sputtered or otherwise deposited on the impermeable membranes 152, to render them visible under fluoroscopy. Preferably, the impermeable membranes 110 are adapted to be breached by the physician or clinician, using a dose escalation pen (or a lancet or stylet as shown in FIGS. 26–31), or some other functionally similar device. The impermeable membranes 152 of the first and second impermeable membrane cans 114, 116 initially seal the first and second semipermeable membranes 120, 124 to prevent any water originating from the patient's implant site from crossing the semipermeable membranes 120, 124 until the impermeable membrane(s) 152 is breached, as shown at 176 in FIGS. 28–31.

Returning now to FIGS. 3–5, the first and second impermeable membrane cans 114, 116 are stacked within the membrane enclosure 112 such that the respective through bores 122, 126 thereof are aligned with the first and second semipermeable membranes 120, 122, respectively. Specifically, the first through bore 122 defined in the first impermeable membrane can 114 is aligned with the first semipermeable membrane 120 and the second through bore 126 defined in the second impermeable membrane can 116 is aligned with the second semipermeable membrane 124. Moreover, the impermeable membrane 152 of the first impermeable membrane can 114 is disposed adjacent the primary water access port 132, whereas the second impermeable can 116 is disposed under the first impermeable membrane can 114 and oriented such that the impermeable membrane thereof is immediately adjacent the first impermeable membrane can 114. Although the present figures show the pump 100 of the present invention equipped with two impermeable membrane cans 114, 116, the present invention is not limited thereto, as a single or a greater number of impermeable membrane cans may be used along with a corresponding number of semipermeable membranes.

Figure 6:
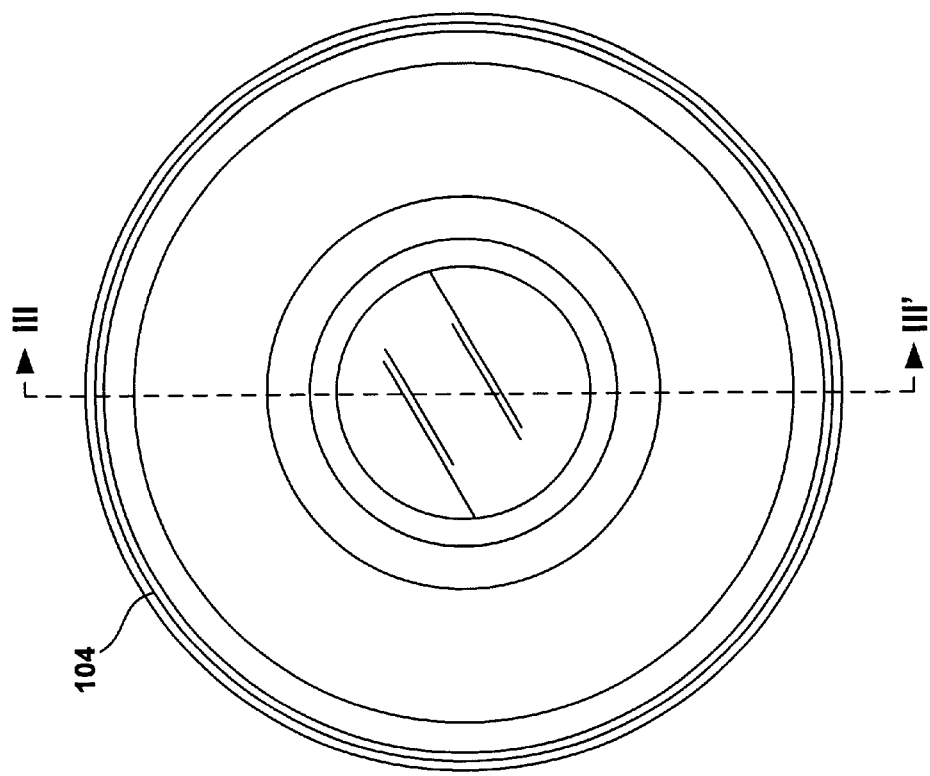
FIG. 6 is a plan view of the second half of the osmotic pump housing, according to an embodiment of the present invention.

FIG. 6 is a plan view of the second half 104 of the osmotic pump housing 101, according to an embodiment of the present invention and FIG. 7 is a cross sectional view thereof, taken along lines III—III'. As shown therein, the second half 104 of the pump housing 101 may have a generally saucer-like shape. Indeed, the second half 104 of the housing 101 may have a generally circular outline and may define a bulge 136 therein to accommodate a portion of the osmotic engine 108 therein. The rim of the second half 104 (See FIG. 10) of the pump housing 101 also defines an indentation 138 adapted to mate with a corresponding feature defined by the rim of the first half 106 of the pump housing 101. FIG. 8 is a perspective view of the first half 106 of the osmotic pump housing 101 according to an embodiment of the present invention, whereas FIG. 9 is a plan view and FIG. 10 is a cross-sectional view thereof, taken along lines IV—IV'.

As shown in the perspective view of FIG. 10, an opening 140 is defined in the also generally saucer-shaped first half 106 of the osmotic pump housing 101. The opening 140 may be centered in the housing half 106 and concentric with the generally circular outline thereof, as shown in FIG. 9. The opening 140 is preferably dimensioned so as to closely fit the membrane enclosure 112. As shown in FIG. 10, the first half 106 of the pump housing 101 may define a bulge 144 that increases the interior volume of the pump 100 when the first and second housing halves 106, 104 are mated to one another.

Figure 12:
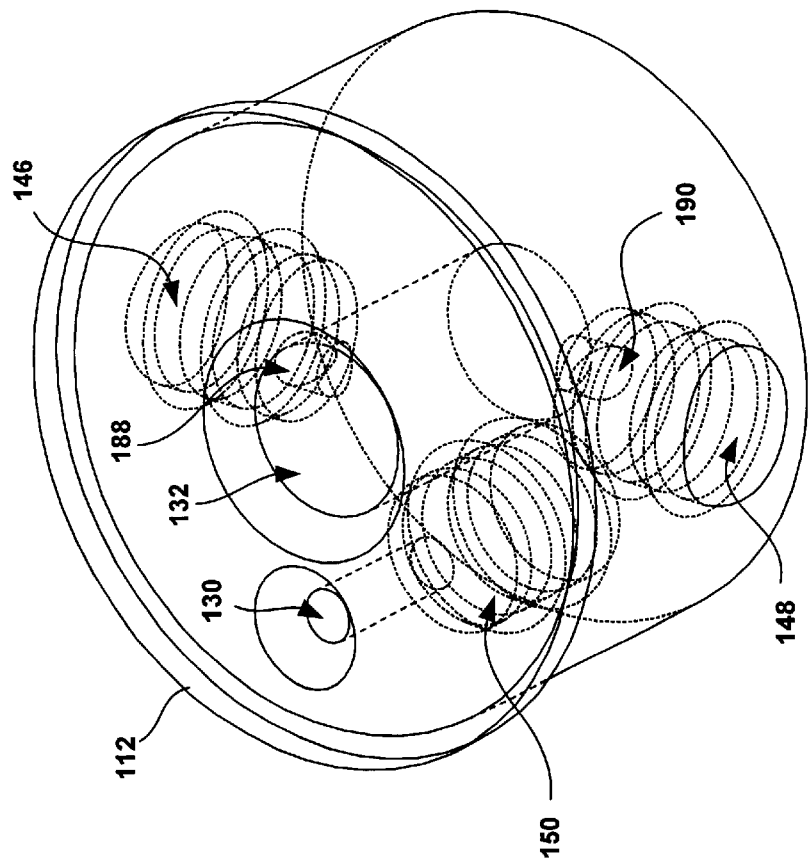
FIG. 12 is a perspective view of the membrane enclosure of FIG. 11, showing the semipermeable membrane wells in dashed lines.
Figure 11:
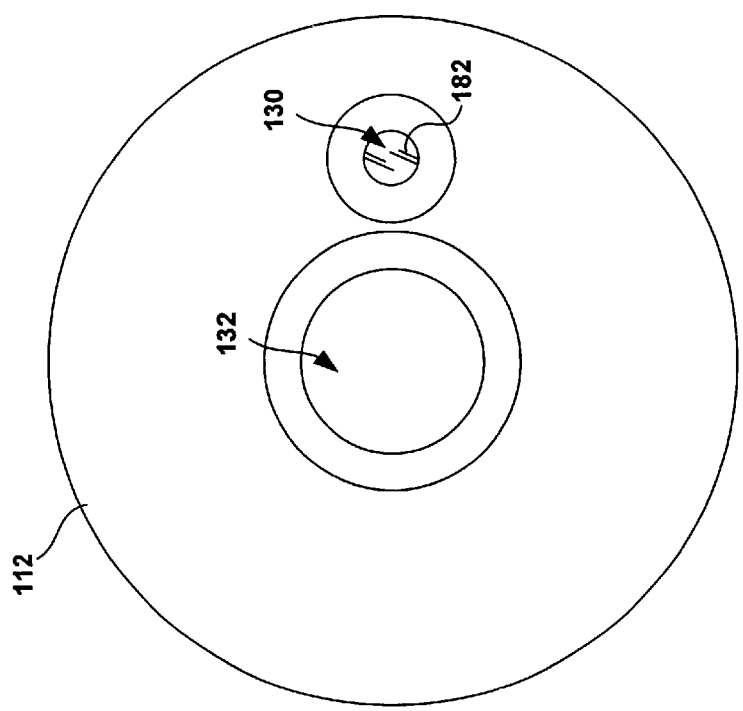
FIG. 11 is a plan view of an embodiment of the membrane enclosure, according to an embodiment thereof.

FIG. 11 is a plan view of an embodiment of the membrane housing 112, according to an embodiment thereof, whereas FIG. 12 is a perspective view of the membrane housing of FIG. 11, showing the semipermeable membrane wells in dashed lines. Considering now FIGS. 11 and 12 collectively, the membrane enclosure 112 may be shaped as a cylinder dimensioned to fit within the osmotic engine 108 and the opening 140 in the first housing half 106. The primary water access port 132 may be a bore partially through the membrane enclosure 112. However, to best control the flow of water form the patient implant site to the osmotic engine 108, the bore defined within the membrane enclosure 112 should not run the entire length of the membrane enclosure 112. Indeed, the only water paths from the implant site to the osmotic engine should be through the initial dose semipermeable membrane well 150, through the first semipermeable membrane well 146 and/or through the second semipermeable membrane well 150. In contrast, the combination of the initial water access port 130 and the initial dose semipermeable well 150 runs the entire length of the membrane enclosure 112, as also shown in FIG. 5. Indeed, once the pump 100 is implanted in the patient and any impermeable membrane that may span the initial water access port 130 is breached, a water path to the osmotic engine 108 may be defined straight through the membrane enclosure 112, as the water from the implant site migrates across the initial dose semipermeable membrane (shown at 134 in FIG. 5) fitted within the initial dose semipermeable membrane well 150.

First and second semipermeable membranes 120, 124 (shown in FIG. 4) are fitted within the first and second semipermeable membrane wells 146, 148, respectively. According to the present invention, when the impermeable membrane 152 of the first impermeable membrane can 114 is breached (as shown at 176 in FIGS. 28, 29 and 31), water from the implant site may enter the primary access port 132 and travel through the first through bore 122 of the first impermeable membrane can 114. From there, the water may travel through a first passageway 188, defined between primary water access port 132 and first semipermeable membrane well 146. After crossing the first semipermeable membrane 120 disposed in the well 146, the water reaches the osmotic engine 108. This first water path is shown at 178 in FIGS. 28, 29 and 31. As the water reaches the osmotic engine 108, the engine 108 swells in volume due to the osmotic pressure differential across the first semipermeable membrane 120 and pushes the piston 160, 162 within the tube-shaped compartment 110 defined within the tube 109 toward the distal end 186 thereof. In so doing, the piston 160, 162 displaces a volume of pharmaceutical agent within the tube-shaped compartment 110, which displaced volume of pharmaceutical agent is delivered out of the distal end 186 of the tube 109. The pharmaceutical agent is delivered at a selected first infusion rate that is related to the thickness, composition and surface area of the first semipermeable membrane 120 and that of the initial dose semipermeable membrane 134.

Similarly, when the impermeable membrane 152 of the second impermeable membrane can 1116 is breached (as shown at 177 in FIGS. 28, 29 and 31), water from the implant site may enter the primary access port 132 and travel through the second through bore 126 of the second impermeable membrane can 116. From there, the water may travel through a second passageway 190, defined within the enclosure 112 between the primary water access port 132 and the second semipermeable membrane well 148. After crossing the second semipermeable membrane 124 disposed in the well 148, the water reaches the osmotic engine 108. This water path is shown at 180 in FIG. 31. As the water reaches the osmotic engine 108, the engine 108 swells in volume due to the osmotic pressure differential across the second semipermeable membrane 124 and pushes the piston 160, 162 within the tube-shaped compartment 110 defined by the tube 109 toward the distal end 186 thereof. In so doing, the piston 160 displaces a volume of pharmaceutical agent within the tube-shaped compartment 110, which displaced volume of pharmaceutical agent is delivered out of the distal end 186 of the tube 109. The pharmaceutical agent is delivered at a selected second infusion rate that is related to the thickness, composition and surface area of the second semipermeable membrane 124, the thickness, composition and surface area of the first semipermeable membrane 120 and the thickness, composition and surface area of the initial dose semipermeable membrane 134. Indeed, the infusion rate of the pump 100 is related to which of the semipermeable membranes 134, 120 and/or 124 are currently exposed to the patient. If only the initial dose semipermeable membrane 134 is exposed to the patient, the infusion rate may be related only to the characteristics of the initial dose semipermeable membrane 134. If both the initial dose semipermeable membrane 134 and the first semipermeable membrane 120 are exposed to the patient, the pump infusion rate may be related to the characteristics of both the initial dose and first semipermeable membranes 134, 120. In other words, the total infusion rate of the pump 100 of the present invention in the state wherein both the initial dose semipermeable membrane 134 and the first semipermeable membrane 120 are breached, may be approximated as the sum of the individual infusion rates contributed by each of the semipermeable membranes 134 and 120. If the initial dose semipermeable membrane 134, the first semipermeable membrane 120 and the second semipermeable membrane 124 are exposed to the patient, the pump infusion rate may be related to the characteristics of the initial dose, the first and the second semipermeable membranes 134, 120 and 124. In other words, the total infusion rate of the pump of the present invention in the state wherein the impermeable membranes 134, 120 and 124 are breached, may be approximated as the sum of the individual infusion rates contributed by each of the semipermeable membranes 134, 120 and 124.

FIG. 17 is a plan view of the coiled tube 109, according to an embodiment of the present invention, FIG. 18 is a cross-sectional view of the tube 109 of FIG. 17, taken along line V—V' and FIG. 19 is a cross-sectional view thereof, taken along line VI—VI'.

According to the present invention, the piston 160 may initially (upon implantation) be disposed within the tube-shaped compartment 110 near the proximal end 184 of the tube 109. As the osmotic engine expands in volume, the only available volume for such expansion is within the tube-shaped compartment 110. Therefore, the expansion of the osmotic engine 108 forces the piston 160 to travel through the coiled tube 109 in the direction of arrow 166, which causes a volume of pharmaceutical agent to be delivered to the patient out of the distal end 186 of the tube 109. A catheter ID (inner diameter) tube 118 may be fitted onto the distal end 186 of the tube 109, which facilitates coupling the catheter 102 thereto. As shown, the tube 109 may be coiled a number of times around the membrane enclosure 112. In the embodiment shown in FIGS. 17–19, the tube 109 is coiled four times around the membrane enclosure 112 (not shown in FIGS. 17–19), although a lesser or greater number of coils may readily be implemented.

FIG. 20 illustrates the tube 109 coupled to a catheter 102, according to an embodiment of the present invention. FIG. 21 illustrates the distal tip of the catheter of FIG. 20, according to an embodiment of the present invention and FIG. 22 illustrates the manner in which the catheter may couple to the catheter ID tube 118. In FIG. 20, the outline of the pump housing 101 is shown for reference purposes. The catheter 102 is used to deliver the pharmaceutical agent from the catheter ID tube 118 to the target area within the patient's body. The catheter 102 may be visible under fluoroscopy over its length, thereby enabling the physician to trim the catheter to the desired length. Alternatively, the catheter 102 may include distal radiopaque markers, for example. As shown in FIG. 21, the distal tip 158 of the catheter 102 may included a rounded, atraumatic tip. A plurality of pharmaceutical agent openings 158 may be defined through the catheter wall, from the internal lumen thereof to the patient. As shown in FIG. 22, the catheter ID may be fitted over the catheter ID tube 118 using a friction fit and/or suitable biocompatible adhesive(s), for example. Any suitable radio opaque material may be used to render all or a portion or selected portions of the catheter 102 radio opaque. For example, the catheter 102 may be formed of silicone or polyurethane and may be doped with barium sulfate, for example. The length of the catheter 102 may be most any therapeutically effective length. A longer length, however, increases the dead space therein and delays the effusion of the pharmaceutical agent into the patient, as it will take longer for the agent to travel the length thereof. For example, the catheter 102 may be about 5 cm to about 100 cm in length. More preferably, the catheter 102 may be about 10 cm to about 30 cm in length. More preferably still, the catheter 012 may be about 15 cm to about 25 cm in length. For example, the catheter 102 may be about 20 cm in length. The internal diameter (ID) of the infusion lumen of the catheter 102 may be selected within the range of about 0.001 inches to about 0.010 inches. The walls of the catheter 102 may be about 0.001 inches to about 0.006 inches in thickness. According to an embodiment of the present invention, the outer diameter (OD) of the catheter 102 may be selected between about 0.024 inches and about 0.066 inches in thickness, for example.

FIGS. 23–25 are cross sections of the tube 109, showing various designs for the piston within the tube shaped compartment 110. Considering now FIGS. 23–25 collectively, the piston of the osmotic pump 100 of the present invention may be spherical, as shown at 160, cylindrical as shown at 162 or may approximate a conical section as shown at 163, although other shapes are possible. A spherical shape minimizes the contact points of the piston 160 with the tube-shaped compartment 110, thereby enabling the piston 160 to travel through the compartment 110, even as the radius of curvature thereof changes form the proximal end 184 to the distal end of the tube 109. Reference 170 represents slurry from the osmotic engine 108. Indeed, reference 170 may be considered to be an extension of the osmotic engine 108, as it swells with water from the patient implant site through the semipermeable membranes 134, 120 and/or 124. As the osmotic engine 108 swells in volume, it exerts a force 168 on the piston 160, 162 or 163, forcing it to travel within the tube-shaped compartment 110 in the direction of arrow 166. In so doing, the piston 160, 162, 163 displaces a corresponding volume of pharmaceutical agent 164. The piston 160, 162, 163 may include stainless steel, nylon or an elastomer, for example. When the piston has a cylindrical shape, as shown on FIG. 24 at 162, the piston 162 may be formed of an elastomeric substance, such as butyl rubber, for example. Such a cylindrical piston 162 may then deform to match the radius of curvature of the tube-shaped compartment 110. The inner diameter of the tube 109 (that is, the diameter of the tube-shaped compartment 110) may be constant over the length of the tube 109 or may become larger or smaller over its length. In the latter case, the piston 163 may assume a truncated conical shape, in which a proximal end thereof is smaller than a distal end thereof (or vice-versa), to match the change in inner diameter of the tube-shaped compartment 110. To prevent the tube 109 from compressing, binding and/or kinking as the osmotic engine 108 swells, the coiled tube 109 may be encased in a hard substance, such as epoxy, for example.

Figures 26, 27, 28:
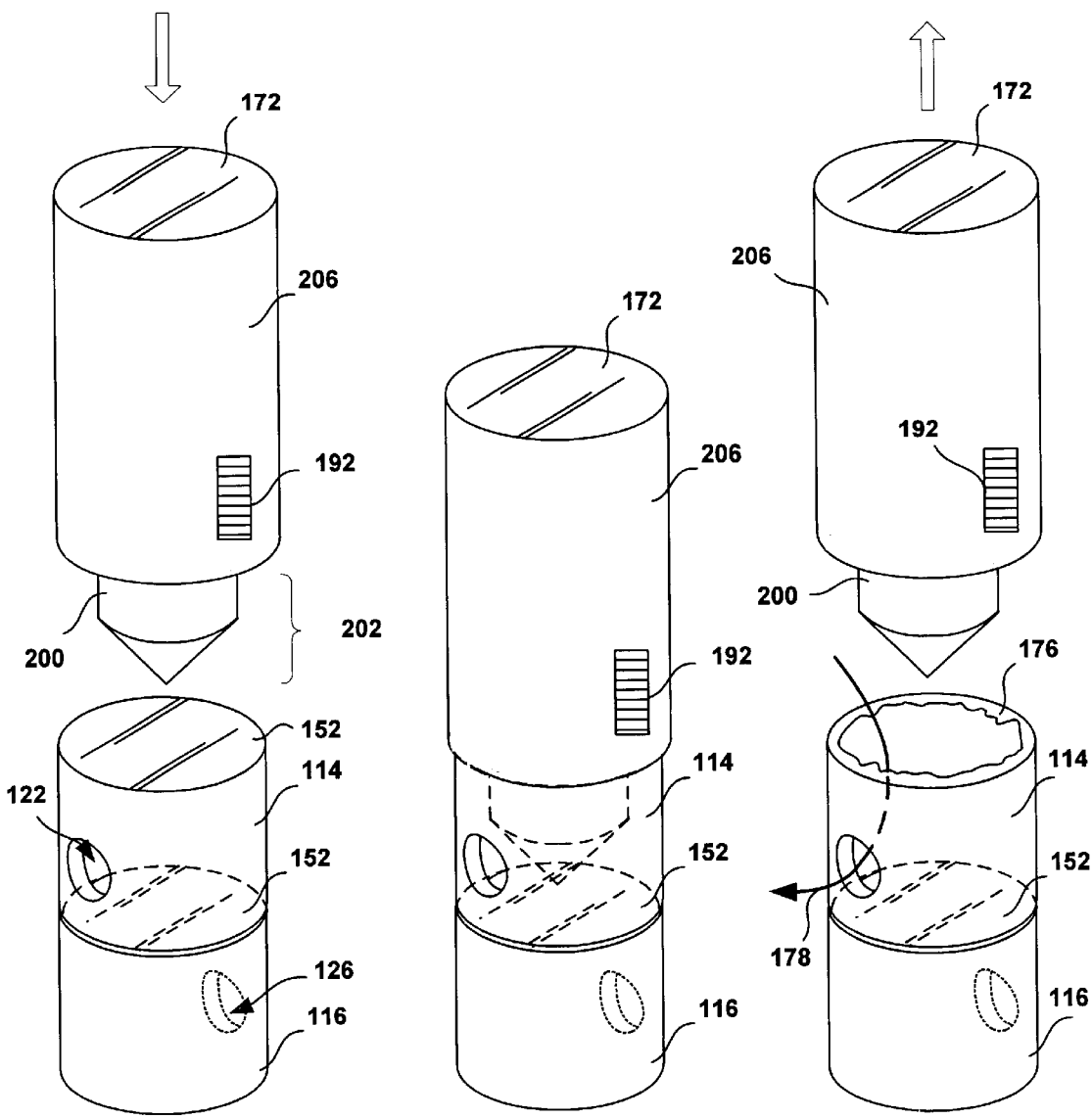
FIG. 26 shows a first step of a method by which the impermeable membrane of the first impermeable membrane may be breached so as to escalate a dose of pharmaceutical agent delivered to the patient, according to an embodiment of the present invention.
FIG. 27 shows a second step of a method by which the impermeable membrane of the first impermeable membrane may be breached so as to escalate a dose of pharmaceutical agent delivered to the patient, according to an embodiment of the present invention.
FIG. 28 shows a third step of a method by which the impermeable membrane of the first impermeable membrane can may be breached so as to escalate a dose of pharmaceutical agent delivered to the patient, according to an embodiment of the present invention.

FIGS. 26–28 shows steps of a method by which the impermeable membrane 152 of the first impermeable membrane can 114 may be breached so as to escalate a dose of pharmaceutical agent delivered to the patient, according to an embodiment of the present invention. FIGS. 29–31 shows further steps of the method by which the impermeable membrane 152 of the second impermeable membrane can 116 may be breached so as to further escalate the dose of pharmaceutical agent delivered to the patient, according to an embodiment of the present invention. While any device may be used to breach the impermeable membranes 152, a dose escalation pen or stylet 172 similar to that shown in FIGS. 26–31 may be advantageously used. An actuator 192, such as a thumb actuated wheel, may be coupled to a pointed extendible portion 200 of the pen 172. Actuating the actuator 192 may cause the pointed and extendible portion 200 to extend in length from a first length 202 shown in FIGS. 26–28, to a second length 204 shown in FIGS. 29–31. At some time after implantation of the pump 100, the patient may require a greater dose of pharmaceutical agent than provided by the initial dose, which initial dose is driven by the osmotic engine 108 swelling in response to water entering the initial water access port 132. Without removing the pump 100 from the patient, the physician may, according to the present invention, use a dose escalation pen or stylet to increase the effusion rate of the pharmaceutical agent from the pump 100 in a simple office or outpatient procedure.

For clarity of illustration, only the first and second impermeable membrane cans 114, 116 of the pump 100 are shown in FIGS. 26–31. In the state illustrated in FIG. 26, the impermeable membranes 152 prevent any water from the patient implant site from reaching the first and second semipermeable membranes 120, 124. When the physician wishes to increase the dose of pharmaceutical agent delivered to the patient, he or she may use the dose escalation pen 172 in a configuration wherein the pointed extendible portion 200 thereof is extended only to the first length 202. By inserting the portion 200 through the patient's skin under fluoroscopic, ultrasonic or manual (palpation) guidance, for example, the physician may breach the impermeable membrane 152 of the first impermeable membrane can 114, as shown at FIG. 27. Preferably, the first length 202 of the extendible portion 200 is selected so as to breach only the impermeable membrane 152 of the first can 114, and not that of the second can 116. Preferably, the outer diameter of the extendible portion 200 is slightly smaller than the outer diameter of the cans 114, 116, to enable the dose escalation pen 172 to create a wide opening when breaching the impermeable membranes 152. Similarly, the handle portion 206 of the pen 172 should have a diameter that is slightly larger than the outer diameter of the cans 114, 116, to limit the travel of the extendible portion 200 within the cans 114, 116. As shown in FIG. 28, once the dose escalation pen 172 is retracted after the impermeable membrane of the first can 114 is breached, a first water path 178 is created, from the patient implant site through the first impermeable membrane can 114, through the first through bore 122 thereof, across the first semipermeable membrane 120 to the osmotic engine 108. In this state of the pump 100, water may now reach the osmotic engine 108 through the initial water access port 132 and through the first impermeable membrane can 114.

Turning now to FIGS. 29–31, when the patient requires an even greater dose of pharmaceutical agent, the physician may actuate the actuator 192 to change the length of the extendible portion 200 to the second length 204, which second length 204 is sufficient to penetrate the first can 114 and breach the impermeable membrane 152 of the second impermeable membrane can 116, as shown at 177 FIG. 31. After the dose escalation pen 172 is retracted as shown at FIG. 31, a second water path 180 is created. The second water path 180 runs from the patient implant site through the first impermeable membrane can 114, through the breached impermeable membrane 152 of the second can 116, through the second through bore 126 of the second can 116, across the second semipermeable membrane 124 to the osmotic engine 108. In this state of the pump 100, water may now reach the osmotic engine 108 through the initial water access port 132, through the first impermeable membrane can 114 as well as through the second impermeable membrane can 116.

The tube-shaped compartment 110 of the pump 100 may be pre-loaded with one or more pharmaceutical agents. 30. For example, the pharmaceutical agent may be therapeutically effective for one or more of the following therapies: pain therapy, hormone therapy, gene therapy, angiogenic therapy, anti-tumor therapy, chemotherapy, allergy therapy, hypertension therapy, antibiotic therapy, bronchodilation therapy, asthmatic therapy, arrhythmia therapy, nootropic therapy, cytostatic and metastasis inhibition therapy, migraine therapy, gastrointestinal therapy and/or other pharmaceutical therapies.

For example, the pharmaceutical agent may include an opioid, a morphine-like agonist, a partial agonist, an agonist-antagonist and/or an alpha 2-adrenoreceptor agonist. Advantageously, the pharmaceutical agent may include morphine, hydromorphone, levorphanol, methadone, fentanyl, sufentanil, buprenorphine, pentazocine and/or butorphanol, for example. The pharmaceutical agent may, for example, include an analgesic agent such as Dihydrocodeine, Hydromorphone, Morphine, Diamorphine, Levorphanol, Butorphanol, Alfentanil, Pentazocine, Buprenorphine, Nefopam, Dextropropoxyphene, Flupirtine, Tramadol, Oxycodone, Metamizol, Propyphenazone, Phenazone, Nifenazone, Paracetamol, Phenylbutazone, Oxyphenbutazone, Mofebutazone, Acetyl Salicylic Acid, Diflunisal, Flurbiprofen, Ibuprofen, Diclofenac, Ketoprofen, Indomethacin, Naproxen, Meptazinol, Methadone, Pethidine, Hydrocodone, Meloxicam, Fenbufen, Mefenamic Acid, Piroxicam, Tenoxicam, Azapropazone, Codein, Bupivacaine, Ketamine, Meperidine and/or [D-Ala2,D-Leu5]enkephalin (DADL). The pharmaceutical agent may also include analgesic that is an alpha-2 adrenergetic agonist such as Clonidine, Tizadine, ST-91, Medetomidine, Dexmedetomidine and/or related alpha-2 adrenergetic agonists. The analgesic may also include an N-methyl-D-aspartate (NMDA) receptor agonist including Dexmethorphan, Ifenprodil, (+)-5-methyl-10,11-dihydro-5H-dibenzo[a,d]-cyclohepten-5,10-imine (MK-801), and/or related NMDA agonists. The analgesic may also include a somatostatin analog selected including Octreotide, Sandostatin, Vapreotide, Lanreotide, and/or related Somatostatin analogs, for example. Alternatively, the pharmaceutical agent may include a non-opioid analgesic such as Ketorolac, super oxide dismutase, baclofen, calcitonin, serotonin, vasoactive intestinal polypeptide, bombesin, omega-conopeptides, and/or related non-opioid analgesics, for example. The pharmaceutical agent in the compartment 310 may be dissolved in an aqueous solution.

For pain therapy, a preferred pharmaceutical agent is Sufentanil. In that case wherein the pharmaceutical agent is (or includes) Sufentanil that is dissolved in an aqueous medium, it has been found that the solubility of the Sufentanil within the aqueous solution increases with increasing acidity of the medium. For example, the pumps according to the present invention may be configured to deliver Sufentanil at up to about 1500 $\mu$g/day, at a concentration of up to about 500,000 $\mu$g/ml, when the Sufentanil is dissolved in an acidic aqueous medium.

EXAMPLE

A pump according to the present invention may include a pharmaceutical agent compartment 310 having a volume of 500 $\mu$l (microliters). A compartment 310 of this volume may contain 500 $\mu$l of pharmaceutical agent solution, the solution including 250,000 $\mu$g of Sufentanil dissolved in an acidic aqueous medium. Therefore, about 1500 $\mu$g/day of such pharmaceutical agent solution may be delivered to the patient over a treatment period spanning about 167 days. Implanted into a patient, such a pump would deliver about 3 $\mu$l of pharmaceutical agent solution to the patient per day, each such 3 $\mu$l of pharmaceutical agent solution containing about 1500 $\mu$l of Sufentanil.

The pharmaceutical agent may also include an anti-allergic agent including Pheniramine, Dimethindene, Terfenadine, Astemizole, Tritoqualine, Loratadine, Doxylamine, Mequitazine, Dexchlorpheniramine, Triprolidine and/or Oxatomide, for example. The pharmaceutical agent may include one or more anti-hypertensive agents, such as Clonidine, Moxonidine, Methyldopa, Doxazosin, Prazosin, Urapidil, Terazosin, Minoxidil, Dihydralalzin, Deserpidine, Acebutalol, Alprenolol, Atenolol, Metoprolol, Bupranolol, Penbutolol, Propranolol, Esmolol, Bisoprolol, Ciliprolol, Sotalol, Metipranolol, Nadolol, Oxprenolol, Nifedipine, Nicardipine, Verapamil, Diltiazim, Felodipine, Nimodipine, Flunarizine, Quinapril, Lisinopril, Captopril, Ramipril, Fosinoprol and/or Enalapril, for example. Alternatively, the pharmaceutical agent may include an antibiotic agent such as Democlocycline, Doxycycline, Lymecycline, Minocycline, Oxytetracycline, Tetracycline, Sulfametopyrazine, Ofloaxcin, Ciproflaxacin, Aerosoxacin, Amoxycillin, Ampicillin, Becampicillin, Piperacillin, Pivampicillin, Cloxacillin, Penicillin V, Flucloxacillin, Erythromycin, Metronidazole, Clindamycin, Trimethoprim, Neomycin, Cefaclor, Cefadroxil, Cefixime, Cefpodoxime, Cefuroxine, Cephalexin and/or Cefradine, for example. Bronchodialotors and anti-asthmatic agents may also be pre-loaded into the tube-shaped compartment 110, including Pirbuterol, Orciprenaline, Terbutaline, Fenoterol, Clenbuterol, Salbutamol, Procaterol, Theophylline, Cholintheophyllinate, Theophylline-ethylenediamine and/or Ketofen, for example. Anti-arrhythmic agents may also be pre-loaded into the pump 100, including Viquidil, Procainamide, Mexiletine, Tocainide, Propafenone and/or Ipratropium, for example. The pharmaceutical agent may alternatively include a centrally acting substance such as Amantadine, Levodopa, Biperiden, Benzotropine, Bromocriptine, Procyclidine, Moclobemide, Tranylcypromine, Tranylpromide, Clomipramine, Maprotiline, Doxepin, Opipramol, Amitriptyline, Desipramine, Imipramine, Fluroxamin, Fluoxetin, Paroxetine, Trazodone, Viloxazine, Fluphenazine, Perphenazine, Promethazine, Thioridazine, Triflupromazine, Prothipendyl, thiothixene, Chlorprothixene, Haloperidol, Pipamperone, Pimozide, Sulpiride, Fenethylline, Methylphenildate, Trifluoperazine, Oxazepam, Lorazepam, Bromoazepam, Alprazolam, Diazepam, Clobazam, Buspirone and/or Piracetam, for example. Cytostatics and metastasis inhibitors may also be pre-loaded within the pump 100 of the present invention, including Melfalan, Cyclophosphamide, Trofosfamide, Chlorambucil, Busulfan, Prednimustine, Fluororacil, Methotrexate, Mercaptopurine, Thioguanin, Hydroxycarbamide, Altretamine and/or Procarbazine, for example. Other pharmaceutical agents that may be pre-loaded include anti-migrane agents such as Lisuride, Methysergide, Dihydroergotamine, Ergotamine and/or Pizotifen or gastrointestinal agents such as Cimetidine, Famotidine, Ranitidine, Roxatidine, Pirenzipine, Omeprazole, Misoprostol, Proglumide, Cisapride, Bromopride and/or Metoclopramide.

The present invention is also a kit, including an implantable osmotic pump 100, a catheter 102 configured to attach to the pump 100 and/or dose escalation pen(s) 172 configured to breach the impermeable membranes 152 of the first and/or second cans 114, 116.

Figure 33:
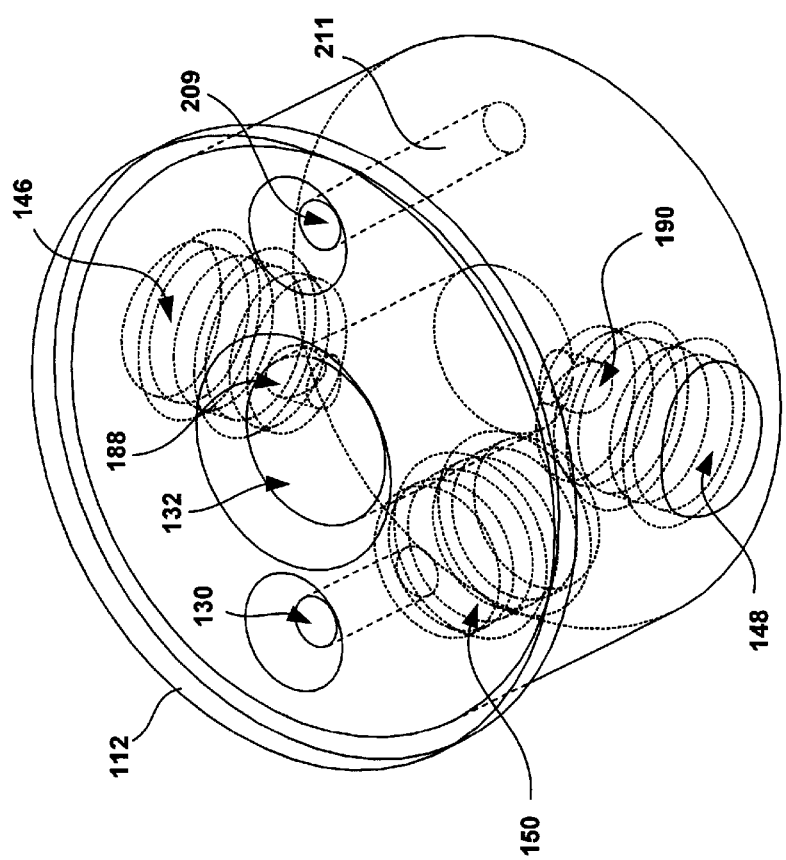
FIG. 33 is a perspective view of the membrane enclosure of FIG. 32, showing the semipermeable membrane wells in dashed lines and the OFF switch feature of the present invention.
Figure 32:
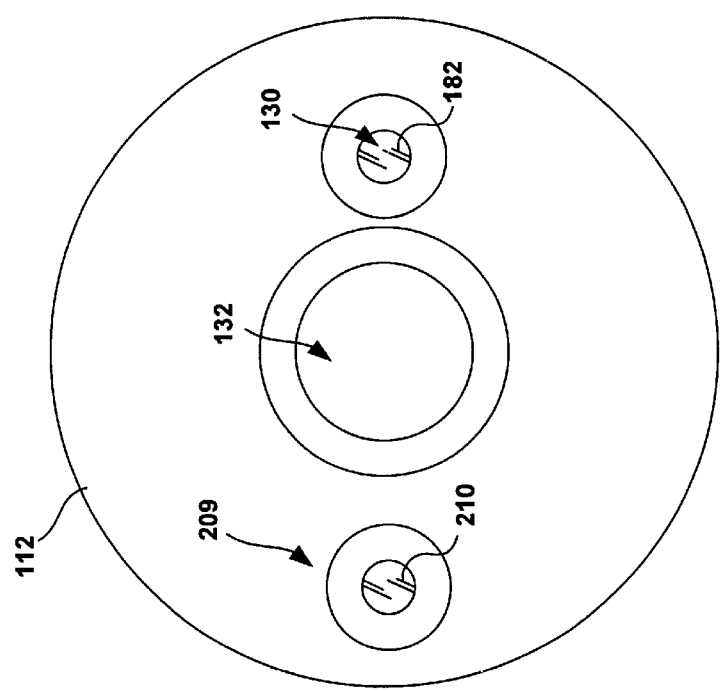
FIG. 32 is a plan view of another embodiment of the membrane enclosure, according to the present invention, showing the OFF feature of the present invention.

There may be instances wherein it is desired to shut the pump down. For example, an adverse reaction to the pharmaceutical agent may have occurred. FIGS. 32 and 33 are plan and perspective views, respectively, of a membrane enclosure 112, according to embodiment of the present invention that addresses this need. As shown therein, the membrane enclosure 112 of FIGS. 32 and 33 is identical to the membrane enclosure of FIGS. 11 and 12, but for the presence of the structure referenced at 209. Reference 209 denotes an OFF switch that is configured to enable the physician to nullify or substantially nullify the osmotic pressure differential across any and all semipermeable membranes such as shown at 120 or 124. The OFF switch 209 includes an OFF switch impermeable membrane 210 and an OFF switch impermeable lumen 211. When and if the OFF switch impermeable membrane 210 is breached, fluid from the patient's implant site flows into the OFF switch lumen 211, bypasses the semipermeable membranes, and flows directly to the osmotic engine 108. Thus, any existing osmotic pressure that may have developed across such semipermeable membranes is reduced to zero or substantially zero, which correspondingly reduces the pump's driving force and reduces the delivery rate of the pharmaceutical agent to zero or about zero. The pump may then be explanted from the patient at will or may simply be left in place.

Figure 34:
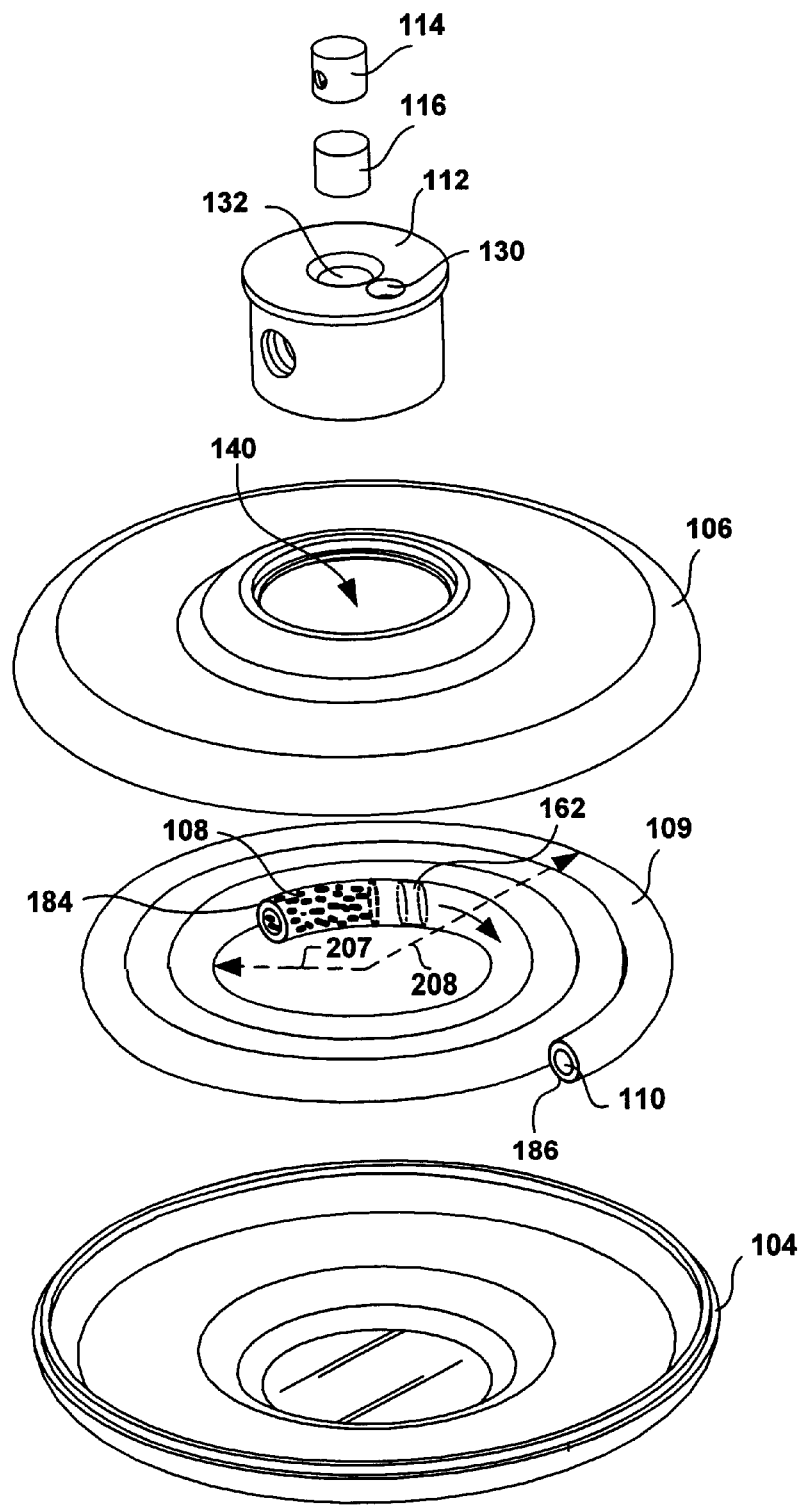
FIG. 34 is an exploded view of another embodiment of an osmotic pump according to the present invention.

FIG. 34 is an exploded view of another embodiment of an osmotic pump according to the present invention. FIG. 34 is similar to FIG. 1, but for the osmotic engine 108. Accordingly, the description of the structures in FIG. 1 that are identical to structures in FIG. 34 is incorporated herein by reference. In FIG. 34, at least a portion of the osmotic engine is disposed within the tube 109, at or near the proximal end 184 thereof. The tube, in this case, is preferably rigid and may be formed of, for example, stainless steel or titanium. In this manner, the expansion of the osmotic engine 108 may be entirely constrained within the tube 109, thereby pushing the piston 162 within the tube 109 toward the proximal end 186 thereof.

FIG. 35 is an exploded view of a three-stage osmotic pump 300, according to another embodiment of the present invention. FIG. 36 is a top view of a three stage osmotic pump according to the present invention, showing the internal structure thereof in dashed lines. FIGS. 37 and 38 are cross-sectional views of a three stage osmotic pump according to the present invention, taken along cross-sectional line IX—IX' and VII—VII' of FIG. 36.

Considering now FIGS. 35–38 collectively, the constituent elements of the pump 300 that are similar to corresponding elements in FIG. 2 are identified by the same reference numerals and the detailed description thereof is omitted here. As shown, the osmotic pump 300 includes a substantially saucer-shaped housing that includes a first housing half 302 and a second housing half 304 that mates with the first housing half 302. In contradistinction to the embodiment shown in FIG. 2, the osmotic pump 300 of FIG. 35 does not include a tube, such as tube 109. Instead, when mated together, the first and second halves 302, 304 of the pump housing together define a tube-shaped and fluid-tight compartment 310 that is adapted to enclose a pharmaceutical agent. The compartment 310 is substantially toroidal in shape, in that it resembles a tube that curves around the osmotic engine 306, following the outer curvature of the pump housing throughout most of its length. The tube-shaped compartment 310 defines a first end 330 that is in fluid communication with the osmotic engine 306 through a passageway 332 and a second end 334 adjacent the compartment outlet 314 that is formed when the first and second halves 302, 304 of the housing are joined together.

Figure 41:
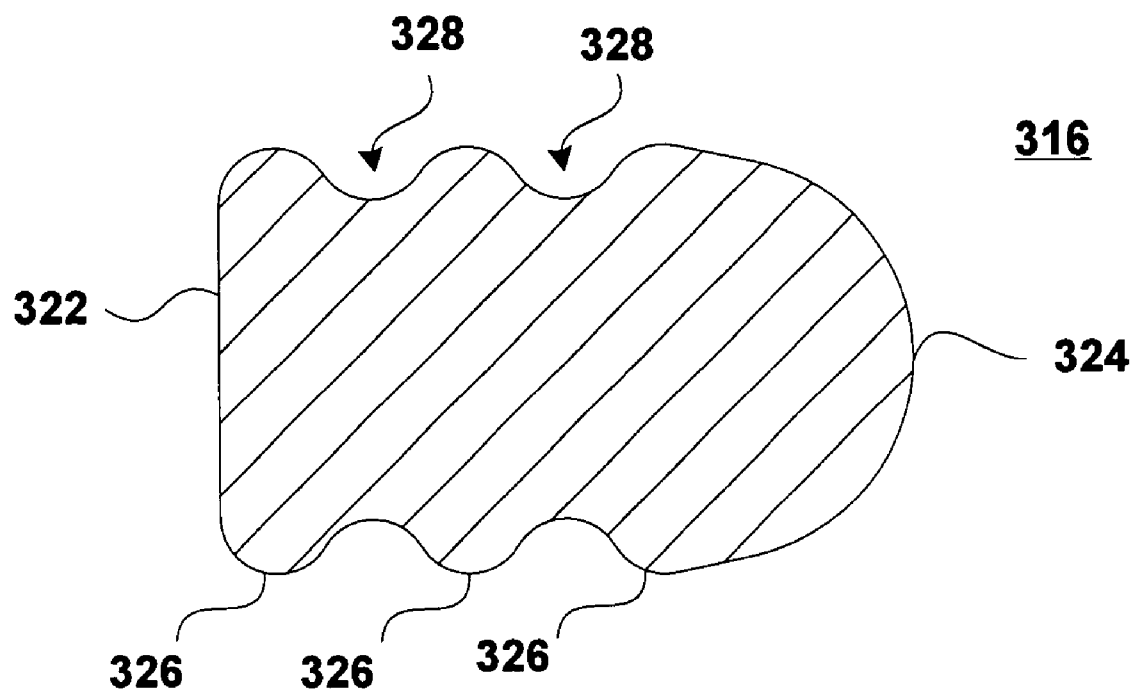
FIG. 41 is a cross-sectional view of a piston, according to an embodiment of the present invention.

The pump 300 includes a piston 316 that is configured and adapted to travel within the compartment 310 in response to the force exerted thereon by the osmotic engine 306. As the piston 316 travels within the compartment 310, it displaces a volume of pharmaceutical agent. The piston 316, when the pump 300 is first implanted, is located adjacent the first end 330 of the compartment 310 and thereafter travels from the first end 330 toward the second end 334, displacing a volume of pharmaceutical agent as it travels. FIG. 41 shows a cross-section of an exemplary embodiment of a piston 316. As shown therein, the piston 316 may define a leading end 322 and a trailing end 324. Additionally, to reduce the surface area of the piston 316 that contacts the wall of the pharmaceutical agent compartment 310, the outer surface of the piston may define one or more throughs 328 and ridges 326, thereby further facilitating the travel of the piston 316 through the compartment 310.

Returning now to FIG. 35, the pump 300, when configured for systemic delivery of a pharmaceutical agent (as is the case wherein the pump is implanted subcutaneously, for example), may include a filter assembly 312. The filter assembly 312 is configured to fit within the compartment outlet 314, so as to maintain the substantially circular footprint of the pump 300, as shown most clearly in FIG. 36. The structure of the filter assembly 312 is further described below, with reference to FIGS. 39 and 40. Functionally, the filter assembly 312 filters the flow of the pharmaceutical agent from the pump 300 to the implant site within the patient or to the aqueous environment in which the pump is deployed. The filter assembly 312 prevents the passage of crystallized pharmaceutical agents to the patient. Crystallized pharmaceutical agents present a danger to the patient, in that the crystallized portion may contain an excess amount of agent and may cause an overdose.

Assuming that the tube-shaped compartment 310 is substantially circular in cross-section, the volume of pharmaceutical agent that may be contained therein may be estimated by:

$$n/360 \; [\tfrac{1}{4}\Pi^2(a+b)(b-a)^2]$$

where, as shown in FIG. 36b (which figure is not shown to the same scale as FIG. 36a), a is the inner radius of the compartment 310, b is the outer radius of the compartment 310 and n represents the number of degrees that the compartment 310 is coiled around the pump 300, as shown by arrow 350. As shown in the embodiment illustrated in FIG. 36b, n is about 270°, as the portion of the compartment 310 that is free to enclose pharmaceutical agent (i.e., from the leading edge 317 of the piston 316 to the proximal edge 313 of the filter assembly 312) spans about ¾ of the circumference of the pump 300.

The pump 300 may also include a ring 308. The ring 308 is preferably formed of the same material as the first and second housing halves 302, 304 such as stainless steel, titanium or alloys thereof, for example. To assemble the pump 300, the piston 316 may be placed adjacent the first end 330 of the compartment 310 and the osmotic engine 306 may be centered between the first and second housing halves 302, 304. The first and second housing halves 302, 304 may then be welded together, along the circumferential seam thereof. The first and second impermeable membrane cans 114, 116 may then be inserted into the membrane enclosure, properly aligned therein and secured thereto. The ring 308 may then be inserted into the central opening formed by the first and second housing halves 302, 304 and the semipermeable membrane enclosure 112, complete with the first and second impermeable cans 114, 116 may then be dropped into the central opening of the ring 308, taking care to align the first through bore 124 with the first semipermeable membrane well 146 and the second through bore 124 with the second semipermeable membrane well 148. The enclosure 112 may then be welded to the ring 308 and the ring 308 may be welded to the first half 302 of the pump housing (not necessarily in that order). The compartment 310 may then be filled with pharmaceutical agent (not shown in FIG. 35) and the filter assembly 312 may thereafter be fitted within the compartment outlet 314 and secured therein. Note that the initial dose semipermeable membrane fitted within the initial dose semipermeable membrane well 336 is not shown in FIGS. 35–38, nor is the first semipermeable membrane fitted within the first semipermeable membrane well 146 or the second semipermeable membrane fitted within the second semipermeable membrane well 148. The membrane enclosure 112 may also incorporate the OFF switch features shown in FIGS. 32 and 33. According to the embodiment of the present invention shown in FIGS. 35–38, the pump 300 is adapted to deliver a pharmaceutical agent or agents at three distinct rates. The first or initial rate occurs when the pump 300 is implanted within the patient and only the initial water access port 130 is in fluid communication with the fluid environment of the pump's implant site within the patient. In this configuration, water from the implant site enters the pump at 130, crosses the initial dose semipermeable membrane in the semipermeable membrane well 336 and comes into contact with the osmotic engine 306, causing the engine 306 to swell and to push the piston 316 toward the second end 334 of the compartment 310 at an initial first rate. Thereafter, the physician may puncture the impermeable membrane of the first can 114, thereby causing water form the implant site to enter therein, cross the first semipermeable membrane within the first semipermeable membrane well 146 and reach the osmotic engine 306. The delivery rate of the pump 300 is now increased from its first, initial rate to a second, larger rate, as more water from the patient implant site is reaching the osmotic engine 306, causing it to swell at a faster rate, thereby causing to piston 316 to travels within the compartment 310 at a corresponding second, faster rate. When the second impermeable membrane can 116 is breached, water from the implant site enters therein, crosses the second semipermeable membrane within the second semipermeable membrane well 148 and reaches the osmotic engine 306. The delivery rate of the pump 300 is now increased from its second rate to a third, even greater rate, as more water from the patient implant site reaches the osmotic engine 306, causing it to swell at a faster rate, thereby causing to piston 316 to travel within the compartment 310 at a third, faster rate, thus displacing a greater amount of pharmaceutical agent than either the initial or second rates.

Figure 39:
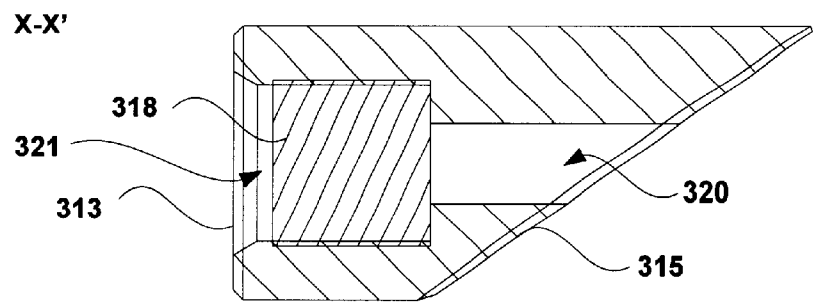
FIG. 39 is a cross-sectional view of the filter assembly 312 of FIG. 35.
Figure 40:
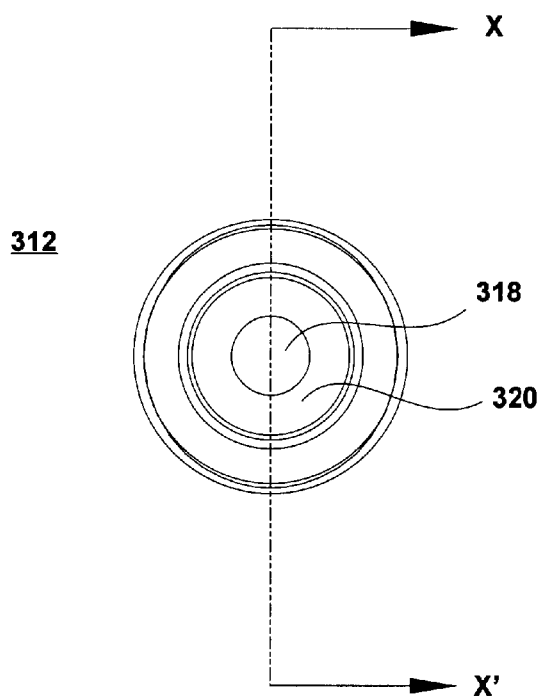
FIG. 40 is a front view of the filter assembly 312 of FIG. 35.

FIG. 39 is a cross-sectional view of the filter assembly 312 of FIG. 35 and FIG. 40 is a front view of the filter assembly 312 of FIG. 35. As shown in FIGS. 35 and 39–40, the filter assembly 312 may be (but need not be) shaped as a slanted and truncated circular cylinder. The filter assembly 312 defines a proximal end 313 and a distal end 315. The assembly 312 further defines a pharmaceutical agent inlet 321 that emerges at the proximal end 313 and a pharmaceutical agent outlet 320 that emerges at the distal end of the filter assembly 312. Between the inlet 321 and the outlet 320, the filter assembly includes a filter 318. According to the present invention, the filter 318 may include a plug of porous material that defines a plurality of pores. The pores, according to an embodiment of the present invention, may range from about 2 microns in average pore size to about 80 microns in average pore size, for example. For example, the average pore size of the porous material of the filter 318 may be selected within the range of about 5 microns to about 20 microns.

The porous material of the filter 318 may be selected to be hydrophilic or hydrophobic, depending upon, for example, the nature of the pharmaceutical agent contained in the pump 300. The pharmaceutical agent in the compartment 310 may be dissolved in an aqueous solution. Alternatively, the pharmaceutical agent in the compartment 310 of the pump 300 may be dissolved in a non-aqueous solution, such as alcohol (benzyl alcohol, for example). In such a case, the filter assembly 318 may include a filter that is substantially hydrophobic in nature, which would allow the passage of a hydrophobic solution, but would not admit the passage of a (or a substantial amount of a hydrophilic solution such as water. Water (or substantial amounts thereof) from the patient implant site, therefore, could not get into the pump 300 and only the pharmaceutical agent could get out, into the patient. Alternatively, the porous material 318 may have hydrophilic characteristics. When the porous material 318 of the filter assembly 312 is hydrophilic, reliance is made on the pressure differential across the porous material 318 (higher on the proximal end 313 than on the distal end 315 end thereof, due to the pressure exerted by the osmotic engine 306) as well as on the pore size of the porous material 318 to limit the diffusion into the pump 300. The pore size may be selected depending upon the magnitude of the pressure differential across the filter assembly 312, the length of the filter 318, the nature of the pharmaceutical agent to be delivered (for example, some pharmaceutical agent including large-sized protein molecules such contained in many pain medications may require a filter 318 defining relatively large size pores) and the aspect ratio of the filter 318 (ratio of aggregate pore size to length of filter 318), among other factors. Suitable materials for the porous material of the filter 318 may be obtained from, for example Millipore Corp. (http://www.millipore.com), Porex Corp. (http//:www.porex.com) and others.

Figure 42:
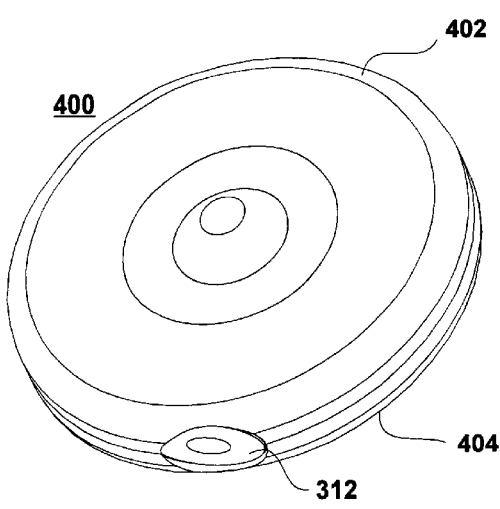
FIG. 42 is a perspective view of a single stage osmotic pump according to another embodiment of the present invention.
Figure 44:
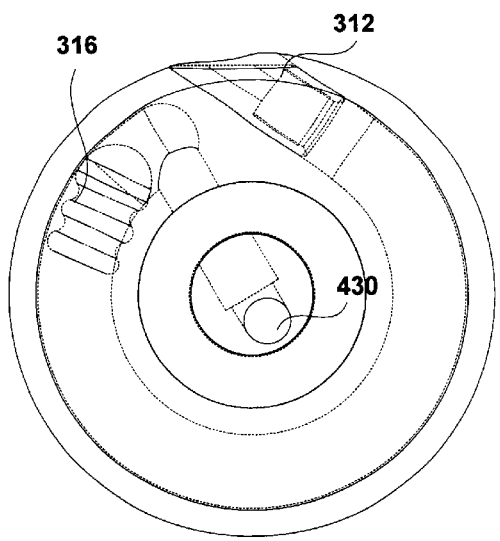
FIG. 44 is a top view of a single stage osmotic pump according to the present invention, showing internal components thereof in dashed lines.
Figure 43:
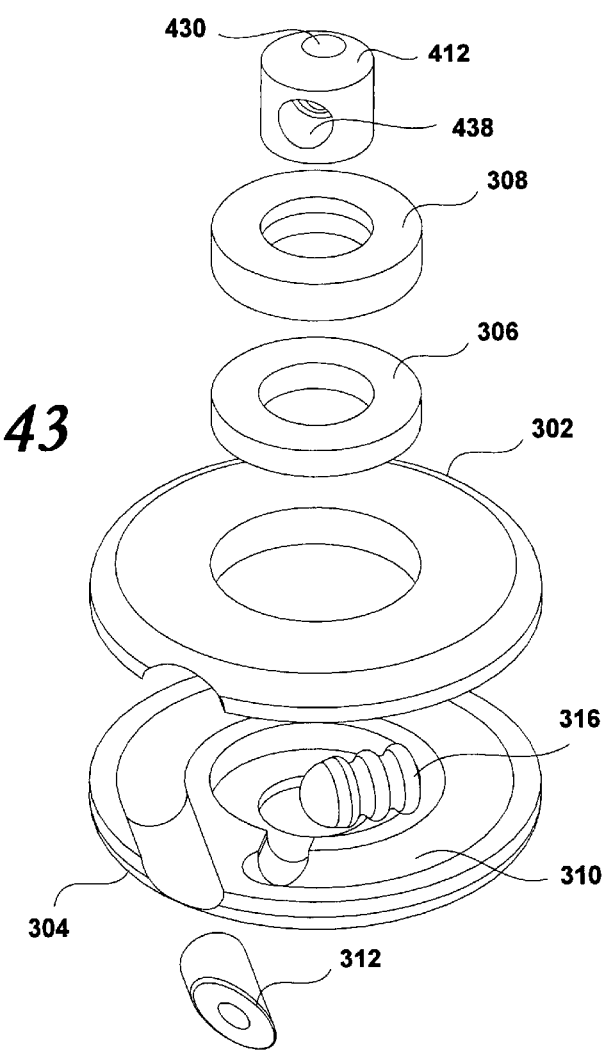
FIG. 43 is an exploded view of a single stage osmotic pump according to the present invention.

FIGS. 42, 43 and 44 show a perspective view, an exploded view and a top view of a single stage osmotic pump according to another embodiment of the present invention, with the top view of FIG. 44 showing internal components thereof in dashed lines. The pump 400 includes first and second housing halves 302, 304, filter assembly 312, piston 316, osmotic engine 306 and ring 308, each of which being similar or identical to those structures in FIGS. 35–38 referenced by the same numerals. A detailed description of these structures is, therefore, omitted here. The single-stage pump 400 may include a semipermeable membrane enclosure 412. The semipermeable membrane enclosure 412 may define a water access port 430 through which water from the patient implant site enters the pump 400. The enclosure 412 also defines a water outlet port 438, thorough which water comes into contact with the osmotic engine 306. Between the water inlet port 430 and the water outlet port 438 is disposed a semipermeable membrane. The water inlet port 430 may be covered by an impermeable membrane of stainless steel or titanium, for example. Moreover, a saturated saline solution may be present between the impermeable membrane covering the water inlet port 430 and the semipermeable membrane within the enclosure 412. Such a saturated saline solution maintains the semipermeable membrane in a hydrated state, and speeds up the initial delivery of the pharmaceutical agent contained in the compartment 310 of the pump 400 once the (optional) impermeable membrane covering the water inlet port 430 is breached. Such an impermeable membrane would be included in the pump 400 only if it was desired to implant the pump 400 in an inactive state and, at some later time, activate it so as to initiate the delivery of the pharmaceutical agent contained therein. The single stage pump 400 may also include the OFF switch features shown in FIGS. 32 and 33.

The pharmaceutical agent compartment of the pumps according to the present invention, as noted above, may contain sufentanil, for example, and may also contain other medications. Depending upon the clinical indication, the pumps according to the present invention may be configured for intravascular, subcutaneous, epidural, intrathecal or intraventricular use. Table 1 below details exemplary maximum expected dosages of Sufentanil for above-listed uses.

TABLE 1

|  | Expected Maximum Dosage of Sufentanil ($\mu$g/day) |
|---|---|
| Intravascular | 1500 |
| Subcutaneous | 1500 |
| Epidural | 500 |
| Intrathecal | 50 |
| Intraventricular | 25 |

Table 2 below shows exemplary delivery schedules for pumps according to the present invention having a diameter of 1.8 cm and a compartment 310 having a capacity of 200 mg, a diameter of 2.8 cm and a compartment 310 having a capacity of 500 mg and a diameter of 5.0 cm and a compartment 310 having a capacity of 2000 mg over selected delivery rates (in mg/day) ranging from 0.50 mg/day to 20.0 mg/day.

| | Exemplary Delivery Schedule Months of Delivery | | |
|---|---|---|---|
| Delivery Rate (mg/day) | 1.8 cm diameter 200 mg capacity (Without dose escalation) | 2.8 cm diameter 500 mg capacity (With dose escalation) | 5.0 cm diameter 2000 mg capacity (With dose escalation) |
| 0.50 | 12 | — | — |
| 0.75 | 8 | 12 | — |
| 2.00 | 3.3 | 6 | — |
| 5.00 | — | 3.3 | 12 |
| 10.0 | — | — | 6 |
| 20.0 | — | — | 3.3 |

The present invention may be implanted under the patient's skin in an outpatient setting. The implantation procedure may be performed with a local anesthetic and may be carried out in as little as 15–20 minutes, for example. Depending upon the implant site, a small 0.5 to 0.75 inch incision may be all that is required, which incision may later be closed with one or more STERI-STRIP® skin closure devices or sutures, for example. The thin, circular shape of the pumps according to the present invention facilitates placement thereof in a number of locations throughout the patient's body, including the chest wall, the lower back, the arms and legs, the neck and even under the scalp, to identify a few exemplary locations. It is to be understood, however, that the above list of possible implant sites is not to be construed as limiting the locations at which the present pumps may be implanted, as those of skill in this art may recognize. The present invention has been presented within the context of pain management and of drugs of a potency comparable to Sufentanil. However, the present invention may be scaled appropriately to deliver any volume of drug at any potency level.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. An implantable osmotic pump for delivering a pharmaceutical agent to a patient, comprising:
   an osmotic engine;
   a substantially toroidal compartment adapted to store a pharmaceutical agent, and a piston disposed within the compartment, the osmotic engine being configured to cause the piston to travel within the compartment and deliver the pharmaceutical agent when the pump is implanted in the patient.

2. The pump of claim 1, further including a tube coiled at least partially around the osmotic engine, an inner lumen of the tube defining the pharmaceutical agent compartment.

3. The pump of claim 2, wherein the tube includes at least one material selected from a group including metals, polymers and polyimid.

4. The pump of claim 1, wherein the compartment is disposed at least partially around the osmotic engine.

5. The pump of claim 2, wherein tube is rigid and wherein the osmotic engine is disposed within the tube.

6. The pump of claim 1, wherein the osmotic engine includes a base, a cylindrical wall attached to the base and a free end opposite the base.

7. The pump of claim 2, further including a housing configured to enclose at least the osmotic engine and the tube.

8. The pump of claim 7, wherein the housing includes a first housing half and a second housing half that mates with the first housing half.

9. The pump of claim 8, wherein each of the first and second housing halves define a saucer shape.

10. The pump of claim 8, wherein each of the first and the second housing halves are substantially circular in shape.

11. The pump of claim 8, wherein the first housing half defines a substantially circular opening.

12. The pump of claim 1, further including a membrane enclosure, the membrane enclosure being partially surrounded by the osmotic engine and including an initial dose semipermeable membrane that is configured to allow water from the patient to reach the osmotic engine when the pump is implanted.

13. The pump of claim 12, wherein the pump is configured to deliver an initial dose of the pharmaceutical agent to the patient at a selected initial infusion rate, the selected initial infusion rate being related to at least one of a thickness, a composition and a surface area of the initial dose semipermeable membrane.

14. The pump of claim 12, wherein the initial dose semipermeable membrane is fitted with an initial dose impermeable membrane that initially seals the initial dose semipermeable membrane.

15. The pump of claim 14, further including a volume of a saturated saline solution between the initial dose semipermeable membrane and the initial dose semipermeable membrane.

16. The pump of claim 12, further including a dose escalation assembly fitted in the membrane enclosure, the dose escalation assembly being adapted to selectively increase an amount of water from the patient that reaches the osmotic engine when the pump is implanted.

17. The pump of claim 16, wherein the dose escalation assembly includes a first impermeable membrane configured to enable water from the patient to reach the osmotic engine through a first fluid path only after being breached.

18. The pump of claim 16, wherein the dose escalation assembly includes:
a first impermeable membrane configured to enable water from the patient to reach the osmotic engine through a first fluid path only after being breached, and
a second impermeable membrane configured to enable water from the patient to reach the osmotic engine through a second fluid path only after being breached, the first path being distinct from the second path.

19. The pump of claim 18, wherein the first and second impermeable membranes are disposed in the membrane enclosure in a stacked configuration wherein the first impermeable membrane must be breached before the second impermeable membrane can be breached.

20. The pump of claim 18, wherein the first fluid path includes a first semipermeable membrane and wherein the second fluid path includes a second semipermeable membrane that is distinct from the first semipermeable membrane.

21. The pump of claim 20, wherein the pump is configured to deliver a first dose of the pharmaceutical agent to the patient at a selected first infusion rate and a second dose of the pharmaceutical agent to the patient at a selected second infusion rate that is greater than the first infusion rate, the selected first and second infusion rates being related to at least one of a thickness, a composition and a surface area of the first and second semipermeable membranes, respectively.

22. The pump of claim 1, wherein the osmotic engine includes a hygroscopic salt.

23. The pump of claim 1, wherein the osmotic engine includes an absorbent polymer.

24. The pump system of claim 23, wherein the absorbent polymer includes a material selected from a group including poly(acrylic acid), potassium salt; poly(acrylic acid), sodium salt; poly(acrylic acid-co-acrylamide), potassium salt; poly(acrylic acid), sodium salt-graft-poly(ethylene oxide); poly (2-hydroxethyl methacrylate); poly(2-hydroxypropyl methacrylate) and poly(isobutylene-co-maleic acid) or derivatives thereof.

25. The pump of claim 1, wherein the compartment has a substantially constant inner diameter over a length thereof.

26. The pump of claim 1, wherein the compartment has a non-constant inner diameter over a length thereof.

27. The pump of claim 2, wherein the tube is coiled at least twice around the osmotic engine.

28. The pump of claim 2, further comprising an epoxy layer encasing at least the tube.

29. The pump of claim 2, wherein the tube includes polyimid.

30. The pump of claim 2, wherein the tube defines a proximal end adjacent the osmotic engine and a distal end at an end opposite the proximal end, and wherein the pump further includes a catheter coupled to the distal end.

31. The pump of claim 30, wherein the catheter and the pump are dimensioned to infuse a volume of up to about 20 µL/day over a treatment period.

32. The pump of claim 30, wherein the catheter and the pump are dimensioned to infuse a dose of Sufentanil of up to 1500 µg/day over a treatment period.

33. The pump of claim 30, wherein the catheter includes a radiopaque tip.

34. The pump of claim 1, wherein the piston includes one of a sphere, an elastomeric cylinder and an elastomeric conical section.

35. The pump of claim 34, wherein the piston includes at least one of stainless steel, a refractory metal, plastic, nylon and rubber.

36. The pump of claim 1, wherein the compartment is pre-loaded with a volume of the pharmaceutical agent.

37. The pump of claim 36, wherein the pharmaceutical agent is therapeutically effective for at least one therapy selected from pain therapy, hormone therapy, gene therapy, angiogenic therapy, anti-tumor therapy, chemotherapy, allergy therapy, hypertension therapy, antibiotic therapy, bronchodilation therapy, asthmatic therapy, arrhythmia therapy, nootropic therapy, cytostatic and metastasis inhibition therapy, migraine therapy, gastrointestinal therapy, schizophrenia therapy, depression therapy, stress therapy and/or other pharmaceutical therapies.

38. The pump of claim 36, wherein the pharmaceutical agent includes an opioid.

39. The pump of claim 36, wherein the pharmaceutical agent includes at least one of a morphine-like agonist, a partial agonist, an agonist-antagonist and an alpha 2-adrenoreceptor agonist.

40. The pump of claim 36, wherein the pharmaceutical agent includes at least one agent selected from a group including morphine, hydromorphone, levorphanol, methadone, fentanyl, sufentanil, buprenorphine, pentazocine and butorphanol.

41. The pump of claim 40, wherein the sufentanil is at a concentration up to about 500,000 µg/mL.

42. The pump of claim 36, wherein the pharmaceutical agent includes an agent selected from a group including Dihydrocodeine, Hydromorphone, Morphine, Diamorphine, Levorphanol, Butorphanol, Alfentanil, Pentazocine, Buprenorphine, Nefopam, Dextropropoxyphene, Flupirtine, Tramadol, Oxycodone, Metamizol, Propyphenazone, Phenazone, Nifenazone, Paracetamol, Phenylbutazone, Oxyphenbutazone, Mofebutazone, Acetyl Salicylic Acid, Diflunisal, Flurbiprofen, Ibuprofen, Diclofenac, Ketoprofen, Indomethacin, Naproxen, Meptazinol, Methadone, Pethidine, Hydrocodone, Meloxicam, Fenbufen, Mefenamic Acid, Piroxicam, Tenoxicam, Azapropazone, Codein, Bupivacaine, Ketamine, Meperidine and DADL.

43. The pump of claim 36, wherein the pharmaceutical agent includes an agent that is an alpha-2 adrenergetic agonist selected from a group including Clonidine, Tizadine, ST-91, Medetomidine, Dexmedetomidine and related alpha-2 adrenergetic agonists.

44. The pump of claim 36, wherein the pharmaceutical agent includes an agent that is an NMDA receptor agonist selected from a group including Dexmethorphan, Ifenprodil, MK-801, and related NMDA agonists.

45. The pump of claim 36, wherein the pharmaceutical agent includes an agent that is a somatostatin analog selected from a group including Octreotide, Sandostatin, Vapreotide, Lanreotide, and related Somatostatin analogs.

46. The pump of claim 36, wherein the pharmaceutical agent includes an agent that is a non-opioid analgesic selected from a group including Ketorolac, super oxide dismutase, baclofen, calcitonin, serotonin, vasoactive intestinal polypeptide, bombesin, omega-conopeptides, and related non-opioid analgesics.

47. The pump of claim 36, wherein the pharmaceutical agent includes an anti-allergic agent selected from a group including Pheniramine, Dimethindene, Terfenadine, Astemizole, Tritoqualine, Loratadine, Doxylamine, Mequitazine, Dexchlorpheniramine, Triprolidine and Oxatomide.

48. The pump of claim 36, wherein the pharmaceutical agent includes an anti-hypertensive agent selected from a group including Clonidine, Moxonidine, Methyldopa, Doxazosin, Prazosin, Urapidil, Terazosin, Minoxidil, Dihydralalzin, Deserpidine, Acebutalol, Alprenolol, Atenolol, Metoprolol, Bupranolol, Penbutolol, Propranolol, Esmolol, Bisoprolol, Ciliprolol, Sotalol, Metipranolol, Nadolol, Oxprenolol, Nifedipine, Nicardipine, Verapamil, Diltiazim, Felodipine, Nimodipine, Flunarizine, Quinapril, Lisinopril, Captopril, Ramipril, Fosinoprol and Enalapril.

49. The pump of claim 36, wherein the pharmaceutical agent includes an antibiotic agent selected from a group including Democlocycline, Doxycycline, Lymecycline, Minocycline, Oxytetracycline, Tetracycline, Sulfametopyrazine, Ofloaxcin, Ciproflaxacin, Aerosoxacin, Amoxycillin, Ampicillin, Becampicillin, Piperacillin, Pivampicillin, Cloxacillin, Penicillin V, Flucloxacillin, Erythromycin, Metronidazole, Clindamycin, Trimethoprim, Neomycin, Cefaclor, Cefadroxil, Cefixime, Cefpodoxime, Cefuroxine, Cephalexin and Cefradine.

50. The pump of claim 36, wherein the pharmaceutical agent includes a bronchodialotors and anti-asthmatic agents selected from a group including: Pirbuterol, Orciprenaline, Terbutaline, Fenoterol, Clenbuterol, Salbutamol, Procaterol, Theophylline, Cholintheophyllinate, Theophylline-ethylenediamine and Ketofen.

51. The pump of claim 36, wherein the pharmaceutical agent includes an anti-arrhythmic agent selected from a group including Viquidil, Procainamide, Mexiletine, Tocainide, Propafenone and Ipratropium.

52. The pump of claim 36, wherein the pharmaceutical agent includes a centrally acting substance selected from a group including Amantadine, Levodopa, Biperiden, Benzotropine, Bromocriptine, Procyclidine, Moclobemide, Tranylcypromine, Tranylpromide, Clomipramine, Maprotiline, Doxepin, Opipramol, Amitriptyline, Desipramine, Imipramine, Fluroxamin, Fluoxetin, Paroxetine, Trazodone, Viloxazine, Fluphenazine, Perphenazine, Promethazine, Thioridazine, Triflupromazine, Prothipendyl, thiothixene, Chlorprothixene, Haloperidol, Pipamperone, Pimozide, Sulpiride, Fenethylline, Methylphenildate, Trifluoperazine, Oxazepam, Lorazepam, Bromoazepam, Alprazolam, Diazepam, Clobazam, Buspirone and Piracetam.

53. The pump of claim 36, wherein the pharmaceutical agent includes a cytostatics and metastasis inhibitor selected from a group including Melfalan, Cyclophosphamide, Trofosfamide, Chlorambucil, Busulfan, Prednimustine, Fluororacil, Methotrexate, Mercaptopurine, Thioguanin, Hydroxycarbamide, Altretamine and Procarbazine.

54. The pump of claim 36, wherein the pharmaceutical agent includes an anti-migrane agent selected from a group including Lisuride, Methysergide, Dihydroergotamine, Ergotamine and Pizotifen.

55. The pump of claim 36, wherein the pharmaceutical agent includes a gastrointestinal agents selected from a group including Cimetidine, Famotidine, Ranitidine, Roxatidine, Pirenzipine, Omeprazole, Misoprostol, Proglumide, Cisapride, Bromopride and Metoclopramide.

56. The pump of claim 16, wherein the dose escalation assembly includes:
a first saturated saline solution between the first impermeable membrane and the first semipermeable membrane, and
a second saturated saline solution between the second impermeable membrane and the second semipermeable membrane.

57. The pump of claim 1, wherein the pharmaceutical agent includes Sufentanil and wherein the pump is configured for:
a daily delivery rate of Sufentanil of up to about 25 micrograms per day when the pump is configured to be implanted intraventricularly;
a daily delivery rate of Sufentanil of up to about 50 micrograms per day when the pump is configured to be implanted intrathecally;
a daily delivery rate of Sufentanil of up to about 500 micrograms per day when the pump is configured to be implanted epidurally;
a daily delivery rate of Sufentanil of up to about 1500 micrograms per day when the pump is configured to be implanted subcutaneously, and
a daily delivery rate of Sufentanil of up to about 1500 micrograms per day when the pump is configured to be implanted intravascularly.

58. A kit, comprising:
an implantable osmotic pump for delivering a pharmaceutical agent to a patient, including an osmotic engine, a tube coiled around the osmotic engine, the tube defining an inner tube-shaped compartment adapted to store a pharmaceutical agent, and a piston disposed within the tube-shaped compartment, the osmotic engine being configured to exert a force on the piston to cause the piston to travel within the tube-shaped compartment and deliver the pharmaceutical agent when the pump is implanted in the patient, and
a catheter configured to attach to the pump.

59. The kit of claim 58, wherein the catheter and the pump are dimensioned to infuse a volume of up to about 20 $\mu$L/day over a treatment period.

60. The kit of claim 58, wherein the catheter and the pump are dimensioned to infuse a dose of Sufentanil of up to about 1500 $\mu$g/day over a treatment period.

61. The kit of claim 58, wherein pump further includes a membrane enclosure, the membrane enclosure being partially surrounded by the osmotic engine and including an initial dose semipermeable membrane that is configured to allow water from the patient to reach the osmotic engine when the pump is implanted.

62. The kit of claim 61, further including a dose escalation assembly fitted in the membrane enclosure, the dose escalation assembly being adapted to selectively increase an amount of water from the patient that reaches the osmotic engine when the pump is implanted.

63. The kit of claim 62, wherein the dose escalation assembly includes:
   a first impermeable membrane configured to enable water from the patient to reach the osmotic engine through a first fluid path only after being breached, and
   a second impermeable membrane configured to enable water from the patient to reach the osmotic engine through a second fluid path only after being breached, the first path being distinct from the second path.

64. The kit of claim 63, further including a dose escalation pen configured to breach at least one of the first and second impermeable membranes.

65. The kit of claim 64, wherein the dose escalation pen includes a dose selection actuator that is adapted to re-configure the dose escalation pen to selectively breach one of the first and second impermeable membranes.

66. The kit of claim 58, wherein the tube-shaped compartment is pre-loaded with the pharmaceutical agent.

67. A method of delivering a pharmaceutical agent to a patient, comprising steps of:
   implanting a pump into the patient, the pump including a pump engine and a compartment adapted to store a pharmaceutical agent, the compartment defining at least a partial torus around the osmotic engine, and
   causing a piston to travel a distance within the compartment and to deliver a dose of pharmaceutical agent out of the compartment, the dose corresponding to the distance traveled by the piston within the compartment.

68. The method of claim 67, wherein the implanting step implants the pump one of intravascularly, subcutaneously, epidurally, intrathecally and intraventricularly.

69. The method of claim 68, wherein the pharmaceutical agent includes Sufentanil and wherein the pump is configured for:
   a daily delivery rate of Sufentanil of up to about 25 micrograms per day when the pump is configured to be implanted intraventricularly;
   a daily delivery rate of Sufentanil of up to about 50 micrograms per day when the pump is configured to be implanted intrathecally;
   a daily delivery rate of Sufentanil of up to about 500 micrograms per day when the pump is configured to be implanted epidurally;
   a daily delivery rate of Sufentanil of up to about 1500 micrograms per day when the pump is configured to be implanted subcutaneously, and a daily delivery rate of Sufentanil of up to about 1500 micrograms per day when the pump is configured to be implanted intravascularly.

70. The method of claim 68, wherein travel of the piston within the compartment causes a delivery of a volume up to about 20 $\mu$L/day over a treatment period.

71. The method of claim 67, further comprising the step of selectively increasing the dose in a stepwise manner over a treatment period without removing the pump from the patient.

72. The method of claim 71, wherein the pump engine includes an osmotic engine and wherein the pump includes an initial dose semipermeable membrane initially exposed to the patient and at least one second semipermeable membrane initially not exposed to the patient and wherein the increasing step includes a step of selectively exposing the at least one second semipermeable membrane to the patient.

73. The method of claim 67, wherein the pump the engine includes an osmotic engine in fluid communication with the piston and wherein the causing step includes a step of increasing a volume of the osmotic engine.

74. A pump, comprising:
   a pump engine;
   a tube coiled around the engine, the tube defining an inner tube-shaped compartment adapted to store a fluid, and
   a piston disposed within the tube-shaped compartment, the engine being adapted to cause the piston to travel within the tube-shaped compartment and to force a dose of the fluid out of the pump.

75. The pump of claim 74, wherein the pump engine includes an osmotic engine.

76. The pump of claim 74, wherein the fluid includes a pharmaceutical agent.

77. The pump of claim 74, further including a catheter coupled to the tube.

78. The pump of claim 74, wherein the pump is fully implantable in a body and wherein pump engine and the tube are enclosed in a biocompatible pump housing.

79. The pump of claim 74, further including a dose escalation assembly, the escalation assembly being configured to selectively increase the dose of fluid delivered.

80. The pump of claim 74, wherein the dose escalation assembly comprises means for increasing the dose delivered in a stepwise manner.

81. The pump of claim 74, wherein the piston includes one of a sphere, an elastomeric cylinder and an elastomeric conical section.

82. An osmotic pump, comprising:
   an osmotic engine, and
   a pump housing enclosing the osmotic engine and defining a substantially toroidal space adapted to contain a volume of pharmaceutical agent.

83. The osmotic pump of claim 82, wherein the pump housing defines a substantially circular outline.

84. The osmotic pump of claim 82, wherein the substantially toroidal space defines an inner and an outer radius, and wherein the osmotic engine is disposed within the inner radius.

85. The osmotic pump of claim 82, further comprising a tube disposed within the toroidal space, the tube defining an inner lumen adapted to contain the volume of pharmaceutical agent.

86. The osmotic pump of claim 82, wherein the pump housing includes a first housing half and a second housing half, the first and second housing halves defining, when mated together, the substantially toroidal space, the substantially toroidal space being fluid tight.

87. The osmotic pump of claim 82, further comprising a semipermeable membrane enclosure and a semipermeable membrane fitted within the semipermeable membrane enclosure.

88. The osmotic pump of claim 87, wherein a single semipermeable membrane is fitted within the semipermeable membrane enclosure and wherein the pump is a single stage pump.

89. The osmotic pump of claim 87, wherein the pump is an n-stage pump and wherein the semipermeable membrane enclosure is fitted with n semipermeable membranes, each of the n stages being configured to be selectively activated after implantation of the pump.

90. The osmotic pump of claim 82, further comprising an OFF switch mechanism configured to be selectively activated after implantation of the pump.

91. The osmotic pump of claim 82, further comprising a filter assembly to filter the pharmaceutical agent.

92. The osmotic pump of claim 91, wherein the filter assembly includes a plug of porous material, the porous material defining pores selected to have an average size of between about 2 microns and about 80 microns.

93. The osmotic pump of claim 91, wherein the filter assembly includes a plug of porous material, the porous material being hydrophilic.

94. The osmotic pump of claim 91, wherein the filter assembly includes a plug of porous material, the porous material being hydrophobic.

95. An implantable osmotic pump, comprising:
   a semipermeable membrane;
   a housing adapted to enclose a volume of pharmaceutical agent and a portion of the semipermeable membrane;
   an osmotic engine adapted to cause the pharmaceutical agent to be delivered out of he pump as an osmotic pressure differential develops across the semipermeable membrane, and
   at least one of:
      an OFF switch, the OFF switch being effective to reduce the osmotic pressure differential across the semipermeable membrane substantially to zero, and
      an ON switch, the ON switch being effective to enable the pump to begin to deliver the pharmaceutical agent out of the pump.

96. The pump of claim 95, wherein the OFF switch includes an OFF switch impermeable membrane and wherein the OFF switch is configured to reduce the osmotic pressure substantially to zero only when the OFF switch impermeable membrane is breached.

97. The pump of claim 96, wherein the OFF switch defines a lumen adapted to allow fluid to bypass the semipermeable membrane when the OFF switch impermeable membrane is breached.

98. The pump of claim 95, wherein the ON switch includes an impermeable membrane disposed over the semipermeable membrane, the pump being adapted to begin delivery of the pharmaceutical agent only after the impermeable membrane is breached.

99. The pump of claim 98, further including a volume of saturated saline solution disposed between the semipermeable membrane and the impermeable membrane.

* * * * *